United States Patent
Forsell

(10) Patent No.: US 10,952,836 B2
(45) Date of Patent: Mar. 23, 2021

(54) VAGINAL OPERATION METHOD FOR THE TREATMENT OF URINARY INCONTINENCE IN WOMEN

(76) Inventor: Peter Forsell, Aegeristrasse (CH)

( * ) Notice: Subject to any disclaimer, the term of this patent is extended or adjusted under 35 U.S.C. 154(b) by 413 days.

(21) Appl. No.: 12/839,115

(22) Filed: Jul. 19, 2010

(65) Prior Publication Data

US 2011/0015473 A1    Jan. 20, 2011

Related U.S. Application Data

(60) Provisional application No. 61/213,818, filed on Jul. 17, 2009.

(30) Foreign Application Priority Data

Jul. 17, 2009    (SE) .................................. 0901005-9

(51) Int. Cl.
*A61F 2/00* (2006.01)
(52) U.S. Cl.
CPC .... *A61F 2/0036* (2013.01); *A61F 2250/0002* (2013.01)
(58) Field of Classification Search
CPC .. A61F 2/04; A61F 2/0036; A61F 2/00; A61F 2/0004; A61F 2/0009; A61F 2/004; A61F 2/0013; A61F 2/0018; A61F 2/0031; A61F 2/0045; A61F 2250/0002; A61F 2002/30668; A61F 2002/3067; A61B 17/29; A61B 17/42
USPC ................................ 600/30, 31, 37; 607/41
See application file for complete search history.

(56) References Cited

U.S. PATENT DOCUMENTS

| | | |
|---|---|---|
| 2,060,913 A | 11/1936 | Weaver |
| 2,795,641 A | 6/1957 | Rowell |
| 3,209,081 A | 9/1965 | Ducote al. |
| 3,598,287 A | 8/1971 | De Man |
| 3,662,758 A | 5/1972 | Glover |
| 3,692,027 A | 9/1972 | Ellinwood, Jr. |
| 3,705,575 A | 12/1972 | Edwards |
| 3,731,679 A | 5/1973 | Wilhelmson et al. |
| 3,731,681 A | 5/1973 | Blackshear et al. |
| 3,750,194 A | 8/1973 | Summers |
| 3,810,259 A * | 5/1974 | Summers ........................ 600/30 |
| 3,817,237 A | 6/1974 | Bolduc |
| 3,855,122 A | 12/1974 | Bourganel |
| 3,863,622 A | 2/1975 | Buuck |
| 3,875,928 A | 4/1975 | Angelchik |
| 3,906,674 A | 9/1975 | Stone |

(Continued)

FOREIGN PATENT DOCUMENTS

| | | |
|---|---|---|
| DE | 19511998 | 10/1996 |
| EP | 0102548 | 3/1984 |

(Continued)

OTHER PUBLICATIONS

U.S. Appl. No. 09/373,224, filed Aug. 12, 1999, Forsell.

(Continued)

*Primary Examiner* — Carrie R Dorna

(57) ABSTRACT

There is disclosed a method for treating urinary incontinence in women. The method comprises accessing the urethra though an incision in the vagina and implanting a restriction device on the urethra or the neck of the urinary bladder. There are also disclosed methods for energizing and controlling the restriction device.

77 Claims, 18 Drawing Sheets

(56) References Cited

U.S. PATENT DOCUMENTS

| | | | |
|---|---|---|---|
| 3,923,060 A | 12/1975 | Ellinwood, Jr. |
| 3,954,102 A | 5/1976 | Buuck |
| 4,003,379 A | 1/1977 | Ellinwood, Jr. |
| 4,009,711 A | 3/1977 | Uson |
| 4,026,305 A | 5/1977 | Brownlee et al. |
| 4,044,401 A | 8/1977 | Guiset |
| 4,201,202 A | 5/1980 | Finney et al. |
| 4,221,219 A | 9/1980 | Tucker |
| 4,235,222 A | 11/1980 | Ionescu |
| 4,243,306 A | 1/1981 | Bonini |
| 4,246,893 A | 1/1981 | Berson |
| 4,265,241 A | 5/1981 | Portner et al. |
| 4,271,827 A | 6/1981 | Angelchik |
| 4,274,407 A | 6/1981 | Scarlett |
| 4,303,225 A | 12/1981 | Freeman |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephen |
| 4,412,530 A | 11/1983 | Burton |
| 4,424,807 A | 1/1984 | Evans |
| 4,426,893 A | 1/1984 | Miller |
| 4,456,175 A | 6/1984 | Mamrosov et al. |
| 4,464,628 A | 8/1984 | Nozawa |
| 4,491,461 A | 1/1985 | Hoekstra |
| 4,505,710 A | 3/1985 | Collins |
| 4,509,947 A | 4/1985 | Lattin |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,559,939 A | 12/1985 | Cobiski |
| 4,563,175 A | 1/1986 | Lafond |
| 4,568,851 A | 2/1986 | Soni et al. |
| 4,583,523 A | 4/1986 | Kleinke et al. |
| 4,584,994 A | 4/1986 | Bamberger et al. |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre |
| 4,628,928 A | 12/1986 | Lowell |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,772 A | 9/1988 | DeWitt |
| 4,771,780 A | 9/1988 | Sholder |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,950,224 A | 8/1990 | Gorsuch et al. |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,098,369 A | 3/1992 | Heilman et al. |
| 5,112,202 A | 5/1992 | Oshima et al. |
| 5,123,428 A | 6/1992 | Schwarz |
| 5,151,082 A | 9/1992 | Gorsuch et al. |
| 5,152,743 A | 10/1992 | Gorsuch et al. |
| 5,160,338 A | 11/1992 | Vincent |
| 5,194,145 A | 3/1993 | Schoendorfer |
| 5,224,926 A | 7/1993 | Gorsuch et al. |
| 5,226,429 A | 7/1993 | Kuzmak |
| 5,250,020 A | 10/1993 | Bley |
| 5,272,664 A | 12/1993 | Alexander |
| 5,297,536 A | 3/1994 | Wilk |
| 5,304,206 A | 4/1994 | Baker, Jr. et al. |
| 5,316,543 A | 5/1994 | Eberbach |
| 5,337,736 A * | 8/1994 | Reddy ............... 600/217 |
| 5,358,474 A | 10/1994 | Kaldany |
| 5,397,354 A | 3/1995 | Wilk et al. |
| 5,415,660 A | 5/1995 | Campbell et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,504,700 A | 4/1996 | Insley |
| 5,505,733 A | 4/1996 | Justin et al. |
| 5,509,888 A | 4/1996 | Miller |
| 5,518,499 A | 5/1996 | Aghr |
| 5,518,504 A | 5/1996 | Polyak |
| 5,540,731 A | 7/1996 | Testerman |
| 5,569,187 A | 10/1996 | Kaiser |
| 5,578,069 A | 11/1996 | Miner, II |
| 5,582,580 A | 12/1996 | Buckman, Jr. et al. |
| 5,665,065 A | 9/1997 | Colman et al. |
| 5,676,674 A | 10/1997 | Bolanos et al. |
| 5,690,108 A | 11/1997 | Chakeres |
| 5,702,431 A | 12/1997 | Wang et al. |
| 5,704,893 A | 1/1998 | Timm |
| 5,735,809 A | 4/1998 | Gorsuch |
| 5,735,887 A | 4/1998 | Barreras et al. |
| 5,738,792 A | 4/1998 | Schoendorfer |
| 5,743,917 A * | 4/1998 | Saxon ............... 128/898 |
| 5,749,909 A | 5/1998 | Schroppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,848,962 A | 12/1998 | Feindt et al. |
| 5,858,001 A | 1/1999 | Tsals et al. |
| 5,876,425 A | 3/1999 | Gord et al. |
| 5,900,909 A | 5/1999 | Parulski et al. |
| 5,902,336 A | 5/1999 | Mishkin |
| 5,910,149 A | 6/1999 | Kuzmak |
| 5,922,026 A * | 7/1999 | Chin ............... A61B 17/0057 606/151 |
| 5,928,195 A | 7/1999 | Malamud et al. |
| 5,938,584 A | 8/1999 | Ardito et al. |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,980,478 A | 11/1999 | Gorsuch et al. |
| 5,995,874 A | 11/1999 | Borza |
| 5,997,501 A | 12/1999 | Gross et al. |
| 6,003,736 A | 12/1999 | Ljunggren |
| 6,034,878 A | 3/2000 | Umemura |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |
| 6,095,969 A * | 8/2000 | Karram et al. ............... 600/31 |
| 6,099,460 A | 8/2000 | Denker |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,145,505 A | 11/2000 | Nikolchev et al. |
| 6,162,238 A | 12/2000 | Kaplan et al. |

(56) References Cited

U.S. PATENT DOCUMENTS

| | | |
|---|---|---|
| 6,185,452 B1 | 2/2001 | Schulman et al. |
| 6,197,055 B1 | 3/2001 | Matthews |
| 6,210,347 B1 | 4/2001 | Forsell |
| 6,215,727 B1 | 4/2001 | Parson et al. |
| 6,221,060 B1 | 4/2001 | Willard |
| 6,233,474 B1 | 5/2001 | Lemelson |
| 6,275,737 B1 | 8/2001 | Mann |
| 6,319,191 B1 | 11/2001 | Sayet et al. |
| 6,321,282 B1 | 11/2001 | Horowitz |
| 6,332,466 B1 | 12/2001 | Yoon |
| 6,346,099 B1 | 2/2002 | Altman |
| 6,377,640 B2 | 4/2002 | Trans |
| 6,400,988 B1 | 6/2002 | Gurewitsch |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,456,883 B1 | 9/2002 | Torgerson et al. |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,464,655 B1 | 10/2002 | Shahinpoor |
| 6,470,892 B1 | 10/2002 | Forsell |
| 6,471,635 B1 | 10/2002 | Forsell |
| 6,471,688 B1 | 10/2002 | Harper et al. |
| 6,475,136 B1 | 11/2002 | Forsell |
| 6,480,946 B1 | 11/2002 | Tomishima |
| 6,482,145 B1 | 11/2002 | Forsell |
| 6,502,161 B1 | 12/2002 | Perego et al. |
| 6,503,189 B1 | 1/2003 | Forsell |
| 6,516,282 B2 | 2/2003 | Hedlund |
| 6,571,127 B1 | 5/2003 | Ben-Haim et al. |
| 6,572,585 B2 | 6/2003 | Choi |
| 6,589,229 B1 | 7/2003 | Connelly et al. |
| 6,600,953 B2 | 7/2003 | Flesler et al. |
| 6,638,208 B1 | 10/2003 | Natarajan et al. |
| 6,638,303 B1 | 10/2003 | Campbell |
| 6,640,309 B2 | 10/2003 | Doblar |
| 6,650,943 B1 | 11/2003 | Whitehurst et al. |
| 6,659,936 B1 | 12/2003 | Furness et al. |
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,745,077 B1* | 6/2004 | Griffith et al. ............ 607/61 |
| 6,772,011 B2 | 8/2004 | Dolgin |
| 6,839,393 B1 | 1/2005 | Sidiropoulos |
| 6,843,766 B1* | 1/2005 | Nemir et al. ............ 600/31 |
| 6,862,479 B1 | 3/2005 | Whitehurst et al. |
| 6,895,280 B2 | 5/2005 | Meadows et al. |
| 6,911,002 B2 | 6/2005 | Fierro |
| 6,915,165 B2 | 7/2005 | Forsell |
| 6,928,338 B1 | 8/2005 | Buchser et al. |
| 6,929,625 B2 | 8/2005 | Bierman |
| 6,948,918 B2 | 9/2005 | Hansen |
| 6,953,429 B2 | 10/2005 | Forsell |
| 6,954,871 B2 | 10/2005 | Kuhn |
| 6,960,233 B1 | 11/2005 | Berg et al. |
| 6,979,351 B2 | 12/2005 | Forsell et al. |
| 7,003,684 B2 | 2/2006 | Chang |
| 7,008,372 B2* | 3/2006 | Chaussy et al. ............ 600/30 |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,165,153 B2 | 1/2007 | Vogt |
| 7,207,936 B2 | 4/2007 | Forsell |
| 7,214,233 B2 | 5/2007 | Gannoe et al. |
| 7,217,236 B2 | 5/2007 | Calderon et al. |
| 7,222,224 B2 | 5/2007 | Woo |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,313,639 B2 | 12/2007 | Perego et al. |
| 7,330,753 B2 | 2/2008 | Policker et al. |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,670,280 B2 | 3/2010 | Gloth |
| 7,844,342 B2 | 11/2010 | Dlugos et al. |
| 7,846,160 B2 | 12/2010 | Payne et al. |
| 7,931,582 B2 | 4/2011 | Forsell |
| 7,972,354 B2 | 7/2011 | Prestezog et al. |
| 7,987,853 B2 | 8/2011 | Swann et al. |
| 7,991,476 B2 | 8/2011 | Nachum |
| 8,070,768 B2 | 12/2011 | Kim et al. |
| 8,096,938 B2 | 1/2012 | Forsell |
| 8,096,939 B2 | 1/2012 | Forsell |
| 8,126,558 B2 | 2/2012 | Forsell |
| 8,195,296 B2 | 6/2012 | Longhini et al. |
| 8,287,444 B2 | 10/2012 | Forsell |
| 8,290,594 B2 | 10/2012 | Forsell |
| 8,313,423 B2 | 11/2012 | Forsell |
| 2001/0011543 A1 | 8/2001 | Forsell |
| 2001/0016738 A1 | 8/2001 | Harrington et al. |
| 2001/0041824 A1 | 11/2001 | Zappala |
| 2002/0022759 A1 | 2/2002 | Forsell |
| 2002/0028980 A1 | 3/2002 | Thierfelder et al. |
| 2002/0040208 A1 | 4/2002 | Flaherty et al. |
| 2002/0055711 A1 | 5/2002 | Lavi et al. |
| 2002/0072698 A1 | 6/2002 | Chiang et al. |
| 2002/0072759 A1 | 6/2002 | Fry |
| 2002/0095139 A1 | 7/2002 | Keogh et al. |
| 2002/0095164 A1 | 7/2002 | Andreas et al. |
| 2002/0099259 A1* | 7/2002 | Anderson et al. ............ 600/29 |
| 2002/0120219 A1 | 8/2002 | Hovland et al. |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009201 A1 | 1/2003 | Forsell |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | Patrick McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0092962 A1 | 4/2003 | Forsell |
| 2003/0088148 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Forsell |
| 2003/0144575 A1 | 7/2003 | Forsell |
| 2003/0144648 A1 | 7/2003 | Forsell |
| 2003/0163029 A1 | 8/2003 | Sonnenschein et al. |
| 2003/0200407 A1 | 10/2003 | Osaka |
| 2003/0208247 A1 | 11/2003 | Spinelli et al. |
| 2003/0231543 A1 | 12/2003 | Matsui |
| 2003/0233143 A1 | 12/2003 | Gharib et al. |
| 2004/0015041 A1 | 1/2004 | Melvin |

(56) References Cited

U.S. PATENT DOCUMENTS

| | | |
|---|---|---|
| 2004/0024285 A1 | 2/2004 | Muckter |
| 2004/0024419 A1 | 2/2004 | Slepian et al. |
| 2004/0034275 A1 | 2/2004 | Forsell |
| 2004/0055610 A1* | 3/2004 | Forsell ............... A61F 2/0036 128/899 |
| 2004/0068299 A1 | 4/2004 | Laske et al. |
| 2004/0089313 A1 | 5/2004 | Utley et al. |
| 2004/0098113 A1 | 5/2004 | Forsell et al. |
| 2004/0098545 A1 | 5/2004 | Pline et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0147886 A1* | 7/2004 | Bonni ............... A61F 2/004 604/327 |
| 2004/0162568 A1 | 8/2004 | Saadat et al. |
| 2004/0177918 A1 | 9/2004 | Murata et al. |
| 2004/0230718 A1 | 11/2004 | Polzin et al. |
| 2004/0236877 A1 | 11/2004 | Burton |
| 2004/0249451 A1 | 12/2004 | Lu et al. |
| 2004/0260316 A1 | 12/2004 | Knudson et al. |
| 2005/0009178 A1 | 1/2005 | Yost et al. |
| 2005/0038484 A1 | 2/2005 | Knudson et al. |
| 2005/0055025 A1 | 3/2005 | Zacouto et al. |
| 2005/0060030 A1 | 3/2005 | Lashinski et al. |
| 2005/0075697 A1 | 4/2005 | Olson et al. |
| 2005/0209633 A1 | 9/2005 | Callister et al. |
| 2005/0222678 A1 | 10/2005 | Lashinski et al. |
| 2005/0238506 A1 | 10/2005 | Mescher et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2005/0276261 A1 | 12/2005 | Kim et al. |
| 2006/0025855 A1 | 2/2006 | Lashinski et al. |
| 2006/0034358 A1 | 2/2006 | Okamura |
| 2006/0069414 A1 | 3/2006 | Imran et al. |
| 2006/0083899 A1 | 4/2006 | Burazin et al. |
| 2006/0127246 A1 | 6/2006 | Forsell |
| 2006/0129028 A1 | 6/2006 | Krakousky |
| 2006/0142635 A1 | 6/2006 | Forsell |
| 2006/0149124 A1 | 7/2006 | Forsell |
| 2006/0149129 A1 | 7/2006 | Watts et al. |
| 2006/0161217 A1 | 7/2006 | Jaax et al. |
| 2006/0167539 A1 | 7/2006 | Mcewan |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0257446 A1 | 11/2006 | Tropsha et al. |
| 2006/0258898 A1* | 11/2006 | Montpetit et al. ............. 600/30 |
| 2007/0015959 A1 | 1/2007 | Forsell |
| 2007/0038232 A1 | 2/2007 | Kraemer |
| 2007/0038831 A1 | 2/2007 | Kim |
| 2007/0049790 A1 | 3/2007 | Wagner et al. |
| 2007/0060788 A1* | 3/2007 | Gellman ............. 600/39 |
| 2007/0073099 A1 | 3/2007 | Forsell |
| 2007/0092862 A1 | 4/2007 | Gerber |
| 2007/0109019 A1 | 5/2007 | Wu |
| 2007/0121389 A1 | 5/2007 | Wu |
| 2007/0156204 A1 | 7/2007 | Denker et al. |
| 2007/0162670 A1 | 7/2007 | Yang |
| 2007/0167670 A1 | 7/2007 | Coleman et al. |
| 2007/0185373 A1* | 8/2007 | Tsonton ............. 600/37 |
| 2007/0193632 A1 | 8/2007 | Shu |
| 2007/0204924 A1 | 9/2007 | Delgiacco et al. |
| 2007/0232848 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfield |
| 2008/0021265 A1* | 1/2008 | Garbin ............. A61B 17/06109 600/30 |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0097487 A1* | 4/2008 | Pool et al. ............. 606/151 |
| 2008/0103544 A1 | 5/2008 | Weiner |
| 2008/0139873 A1 | 6/2008 | Peters et al. |
| 2008/0154256 A1 | 6/2008 | Payne et al. |
| 2008/0178889 A1 | 7/2008 | Tal |
| 2008/0195172 A1* | 8/2008 | Furness et al. ............. 607/41 |
| 2008/0200753 A1 | 8/2008 | Forsell |
| 2008/0214888 A1 | 9/2008 | Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0082705 A1 | 3/2009 | Asfora |
| 2009/0131959 A1 | 5/2009 | Rolland |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0145138 A1 | 6/2010 | Forsell |
| 2010/0145139 A1 | 6/2010 | Forsell |
| 2010/0217067 A1 | 8/2010 | Forsell |
| 2010/0286735 A1 | 11/2010 | Garfield et al. |
| 2010/0305656 A1 | 12/2010 | Imran et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Tal |
| 2010/0318117 A1 | 12/2010 | Forsell |
| 2010/0318118 A1 | 12/2010 | Forsell |
| 2010/0324360 A1 | 12/2010 | Forsell |
| 2010/0324361 A1 | 12/2010 | Forsell |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015474 A1 | 1/2011 | Forsell |
| 2011/0040143 A1 | 2/2011 | Forsell |
| 2011/0066254 A1 | 3/2011 | Forsell |
| 2011/0087337 A1 | 4/2011 | Forsell |
| 2011/0172693 A1 | 7/2011 | Forsell |
| 2011/0184230 A1 | 7/2011 | Forsell |
| 2011/0192402 A1 | 8/2011 | Forsell |
| 2011/0196192 A1 | 8/2011 | Forsell |
| 2011/0196193 A1 | 8/2011 | Forsell |
| 2011/0196194 A1 | 8/2011 | Forsell |
| 2011/0196271 A1 | 8/2011 | Forsell |
| 2011/0196371 A1 | 8/2011 | Forsell |
| 2011/0196391 A1 | 8/2011 | Forsell |
| 2011/0196411 A1 | 8/2011 | Forsell |
| 2011/0196435 A1 | 8/2011 | Forsell |
| 2011/0196466 A1 | 8/2011 | Forsell |
| 2011/0196476 A1 | 8/2011 | Forsell |
| 2011/0196481 A1 | 8/2011 | Forsell |
| 2011/0196482 A1 | 8/2011 | Forsell |
| 2011/0196483 A1 | 8/2011 | Forsell |
| 2011/0196484 A1 | 8/2011 | Forsell |
| 2011/0196485 A1 | 8/2011 | Forsell |
| 2011/0196486 A1 | 8/2011 | Forsell |
| 2011/0196505 A1 | 8/2011 | Forsell |
| 2011/0196506 A1 | 8/2011 | Forsell |

(56) References Cited

U.S. PATENT DOCUMENTS

| | | |
|---|---|---|
| 2011/0201870 A1 | 8/2011 | Forsell |
| 2011/0201871 A1 | 8/2011 | Forsell |
| 2011/0201873 A1 | 8/2011 | Forsell |
| 2011/0202041 A1 | 8/2011 | Forsell |
| 2011/0202129 A1 | 8/2011 | Forsell |
| 2011/0202131 A1 | 8/2011 | Forsell |
| 2011/0208231 A1 | 8/2011 | Forsell |
| 2011/0218394 A1 | 9/2011 | Forsell |
| 2011/0224787 A1 | 9/2011 | Forsell |
| 2011/0230930 A1 | 9/2011 | Forsell |
| 2011/0263928 A1 | 10/2011 | Forsell |
| 2012/0029550 A1 | 2/2012 | Forsell |

FOREIGN PATENT DOCUMENTS

| | | |
|---|---|---|
| EP | 01 343 40 | 3/1985 |
| EP | 0 200 286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0626154 | 11/1994 |
| EP | 0876808 | 11/1998 |
| EP | 1 004 330 | 5/2000 |
| EP | 1 033 142 | 9/2000 |
| EP | 1 072 238 | 1/2001 |
| EP | 1 514 526 | 3/2005 |
| EP | 1563814 | 8/2005 |
| EP | 1563866 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 884 259 A1 | 2/2008 |
| EP | 1 913 880 | 4/2008 |
| FR | 2621248 A1 | 7/1989 |
| FR | 2688693 | 9/1993 |
| FR | 2692777 | 12/1993 |
| FR | 2756485 | 6/1998 |
| FR | 2797181 | 2/2001 |
| FR | 2908979 | 5/2008 |
| GB | 8 856 74 | 12/1961 |
| GB | 1194358 | 6/1970 |
| WO | WO 84/01282 | 4/1984 |
| WO | WO 91/00094 | 1/1991 |
| WO | WO 94/27504 | 12/1994 |
| WO | WO 96/01597 | 1/1996 |
| WO | WO 96/11036 | 4/1996 |
| WO | WO 96/39932 | 12/1996 |
| WO | WO 97/41799 | 11/1997 |
| WO | WO 98/50099 | 11/1998 |
| WO | WO 99/18885 | 4/1999 |
| WO | WO 00/09047 | 2/2000 |
| WO | WO 00/09048 | 2/2000 |
| WO | WO 00/15158 | 3/2000 |
| WO | WO 00/16686 | 3/2000 |
| WO | WO 00/33825 | 6/2000 |
| WO | WO 01/12078 | 2/2001 |
| WO | WO 01/12108 | 2/2001 |
| WO | WO 01/45487 | 6/2001 |
| WO | WO 01/45590 | 6/2001 |
| WO | WO 01/47431 | 7/2001 |
| WO | WO 01/47575 | 7/2001 |
| WO | WO 0147434 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | WO 02/38217 | 5/2002 |
| WO | WO 02/40083 | 5/2002 |
| WO | WO 02/053210 | 7/2002 |
| WO | WO 02/058563 | 8/2002 |
| WO | WO 02/087657 | 11/2002 |
| WO | WO 02/100481 | 12/2002 |
| WO | WO 03/002192 | 1/2003 |
| WO | WO 03/033054 | 4/2003 |
| WO | WO 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 98/06358 | 2/2005 |
| WO | WO 2005/072169 | 8/2005 |
| WO | WO 2005/105003 | 11/2005 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 0147435 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

U.S. Appl. No. 11/988,450, filed May 27, 2009, Forsell.
"NPC-102 N Medical Angioplasty Sensor" web page at www.novasensor.com/catalog/NPC_102.html and NPC-102 Datasheet, circa 1997, retrieved from the Internet Archives for www.novasensor.com.
Webster's II New River side University, 1984, pp. 573,1000.
U.S. Appl. No. 13/122,907, Forsell; 2011-0196466; filed Aug. 11, 2011; N&V Ref: 5613-66.
U.S. Appl. No. 13/123,019, Forsell; 2011-0196411; filed Aug. 11, 2011; N&V Ref: 5613-61.
U.S. Appl. No. 13/123,025, Forsell; 2011-0218394; filed Sep. 8, 2011; N&V Ref: 5613-62.
U.S. Appl. No. 13/123,037, Forsell; 2011-0201873; filed Aug. 18, 2011; N&V Ref: 5613-65.
U.S. Appl. No. 13/123,041, Forsell; 2011-0263928; filed Oct. 27, 2011; N&V Ref: 5613-36.
U.S. Appl. No. 13/123,082, Forsell; 2011-0196194; filed Aug. 11, 2011; N&V Ref: 5613-35.
U.S. Appl. No. 13/123,151, Forsell; 2011-0196476; filed Aug. 11, 2011' N&V Ref: 5613-43.
U.S. Appl. No. 13/123,182, Forsell; 2011-0196481; filed Aug. 11, 2011; N&V Ref: 5613-44.
U.S. Appl. No. 13/123,197, Forsell; 2011-0196482; filed Aug. 11, 2011; N&V Ref: 5613-45.
U.S. Appl. No. 13/123,145, Forsell; 2011-0230930; filed Sep. 22, 2011; N&V Ref: 5613-56.
U.S. Appl. No. 13/123,183, Forsell; 2011-0196271; filed Aug. 11, 2011; N&V Ref: 5613-58.
U.S. Appl. No. 13/123,231, Forsell; 2011-0201870; filed Aug. 18, 2011; N&V RefL 5613-55.
U.S. Appl. No. 13/123,232, Forsell; 2011-0196483; filed Aug. 11, 2011; N&V Ref: 5613-54.
U.S. Appl. No. 13/123,255, Forsell; 2011-0196486; filed Aug. 11, 2011; N&V Ref: 5613-72.
U.S. Appl. No. 13/123,261, Forsell; 2011-0196391; filed Aug. 11, 2001; N&V Ref: 5613-73.
U.S. Appl. No. 13/123,284, Forsell; 2011-0196192; filed Aug. 11, 2011; N&V Ref: 5613-47.
U.S. Appl. No. 13/123,330, Forsell; 2011-0192402; filed Aug. 11, 2011; N&V Ref: 5613-37.
U.S. Appl. No. 13/123,394, Forsell; 2011-0196485; filed Aug. 11, 2011; N&V Ref: 5613-50.
U.S. Appl. No. 13/123,402, Forsell; 2011-0196484; filed Aug. 11, 2011; N&V Ref: 5613-52.

(56) References Cited

OTHER PUBLICATIONS

U.S. Appl. No. 13/123,425, Forsell; 2011-0208231; filed Aug. 25, 2011; N&V Ref: 5613-28.
U.S. Appl. No. 13/123,436, Forsell; 2011-0196193; filed Aug. 11, 2011; N&V Ref: 5613-53.
U.S. Appl. No. 13/123,446, Forsell; 2011-0202131; filed Aug. 18, 2011; N&V Ref: 5613-51.
U.S. Appl. No. 13/123,536, Forsell; 2011-0196371; filed Aug. 11, 2011; N&V Ref: 5613-74.
U.S. Appl. No. 13/123,537, Forsell; 2011-0196435; filed Aug. 11, 2011' N&V Ref: 5613-75.
U.S. Appl. No. 13/123,583, Forsell; 2011-0202041; filed Aug. 18, 2011; N&V Ref: 5613-26.
U.S. Appl. No. 13/123,586, Forsell; 2011-0224787; filed Sep. 15, 2011; N&V Ref: 5613-49.
U.S. Appl. No. 13/123,587, Forsell; 2011-0201871; filed Aug. 18, 2011; N&V Ref: 5613-48.
U.S. Appl. No. 13/123,667, Forsell; 2011-0202129; filed Aug. 18, 2011; N&V Ref: 5613-46.
Anand, Sneh. "Electrical Pacing of the Ampullary Isthmic Junction for Contraception", IEEE Engineering in Medicine & Biology $10^{th}$ Annual International Conference, 1988.

\* cited by examiner

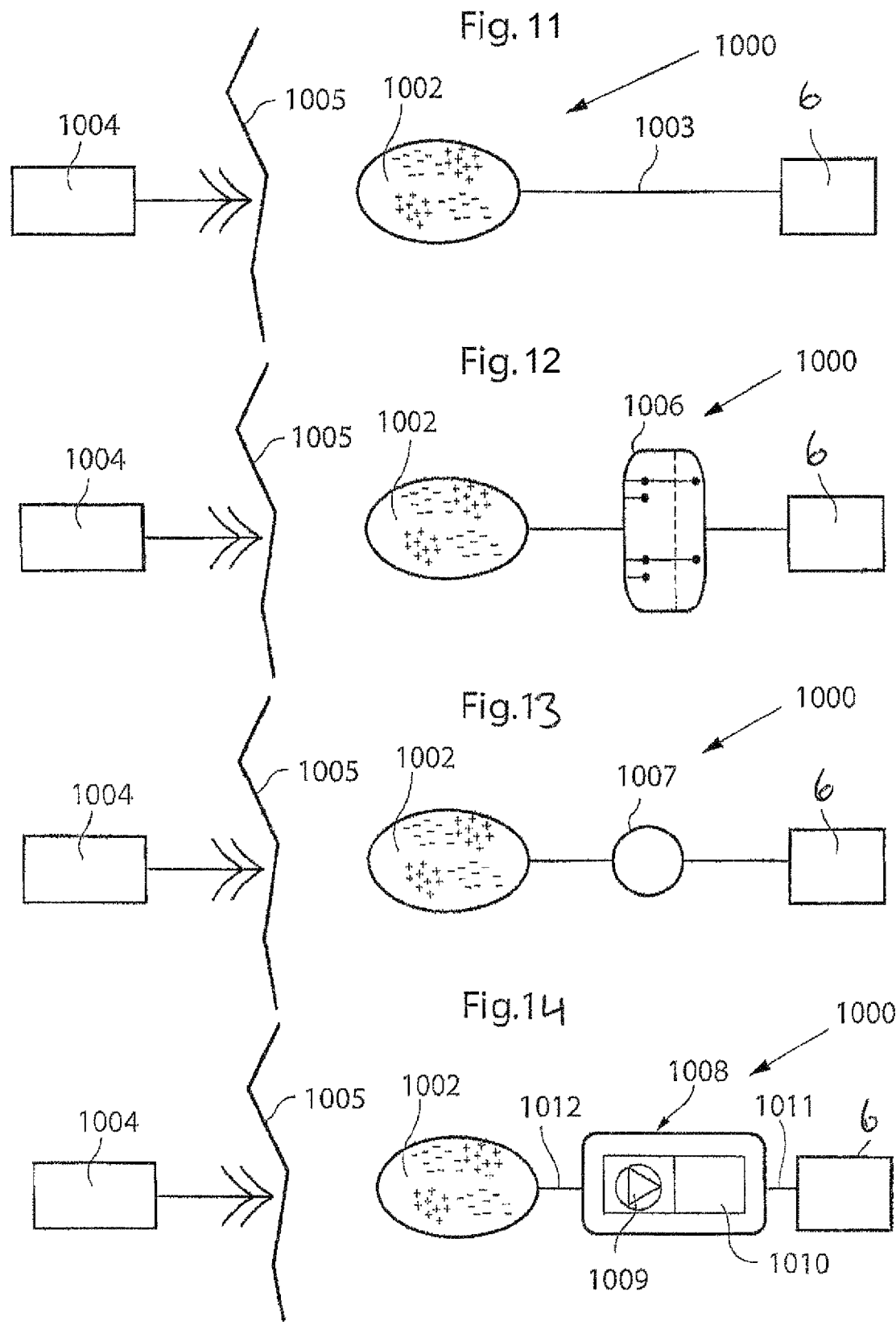

VAGINAL OPERATION METHOD FOR THE TREATMENT OF URINARY INCONTINENCE IN WOMEN

This application claims the benefit of U.S. Provisional Application No. 61/213,818, filed Jul. 17, 2009, and claims priority to Swedish Application No. SE 0901005-9, filed Jul. 17, 2009, the entire contents of each of which are hereby incorporated by reference.

FIELD OF THE INVENTION

The present invention relates to the treatment of female patients suffering from urine incontinence.

BACKGROUND

Urine incontinence is a widespread problem among women which severely lowers the quality of life of those affected. Different surgical, pharmacological and other approaches are available for treating urinary incontinence. For example, several surgical procedures relates to stabilizing the urethra and/or the bladder in order to improve the physiological ability to hold urine. One of the most commonly used methods is applying a sling under the urethra, thus lifting and stabilizing it (Koch Y K, Zimmern F, Curr Opin Urol 2008 July; 18(4):370-6).

In the context of treating urine incontinence in women, it is previously known that the urethra can be accessed through the vagina in order to for instance 1) place a staple into the pelvic bone that lifts and supports the bladder and the urethra (WO 92/16152) 2), Inserting a sling that supports the urethra (U.S. Pat. No. 6,641,524), and 3) inserting a shaft that guides a sling that is anchored and supports the bladder (US 2008/0125621 A1). In addition, there has been described a method whereby a device that is adapted to apply pressure to the urethra is placed in the vagina in order to apply pressure from inside the vagina as to prevent the flow of urine.

In addition, it has been described how urine incontinence can be treated by placing a restriction device on the urethra (for example U.S. Pat. No. 4,571,749).

Manually operated urine incontinence treatment devices having an artificial hydraulic sphincter device engaging the urethra are previously known. These may be connected to an elastic reservoir implanted in the region of the labia major. A disadvantage of this prior apparatus is that over time hard fibrosis is developed around the reservoir that may cause malfunction of pumping components. Furthermore, it is a rather cumbersome task to manually squeeze the elastic implanted reservoir to pump hydraulic fluid to open the sphincter device when the patient needs to urinate. In particular, women may get urine on their hands. A device with the advantage that it has a power operated adjustment device has also been described (WO 01/45486).

Even though some of the mentioned methods are used today there is still a need for improved methods for treating urine incontinence in women.

SUMMARY OF THE INVENTION

It is an object of the present invention to obviate at least some of the disadvantages in the prior art. A method for treating a female urinary incontinent patient is provided, the method comprising the steps of: a) accessing the urethra and/or the neck of the urinary bladder trough an opening in the vaginal wall of the patient, b) dissecting in the patient at least a part of the urethra and/or the neck of the urinary bladder, c) implanting at least one restriction device in a position that enables it to at least partially restrict the flow of urine through the urethra and/or the neck of the urinary bladder, wherein said restriction device is used to decrease the cross sectional area of the urine passageway in order to stop or decrease the flow of urine through said urine passageway.

The restriction device is preferably powered and the method thus includes an energy source and preferable placing an energy receiving device within the body.

One advantage of the present invention is that is does not require manual manipulation of a combined reservoir and pump mechanism placed in the region of the labia major of the patient.

Another advantage of the invention is that it does not involve complicated surgery.

The invention comprises a method for surgery to be performed on a patient suffering from urinary incontinence whereby the urethra is accessed trough an incision in the vaginal wall of the patient.

A first preferred method for treating a female urinary incontinent patient, the method comprising the steps of;
 a) accessing any of the urethra and the neck of the urinary bladder trough an opening in the vaginal wall of the patient,
 b) dissecting in the patient at least a part of any of the urethra and the neck of the urinary bladder,
 c) implanting at least one restriction device in a position that enables it to decrease the cross-sectional area of the urine passageway to at least partially restrict the flow of urine through any of the urethra and the neck of the urinary bladder.

A second preferred method involving a vaginal approach for operating urinary incontinence comprises the steps of:
 a. inserting a tube or needle trough an opening in the vaginal wall of the patient into the body of the patient,
 b. using said tube or needle to insufflate a site in a surrounding of at least one organ selected from group consisting of: a) the urethra, b) the neck of the urinary bladder c) fibrotic tissue surrounding said organs and d) the muscles surrounding said organs, of the body of the patient with a gas,
 c. inserting at least two laparoscopic trocars into said site,
 d. inserting at least one camera trough at least one of said at least two laparoscopic trocars, and
 e. inserting at least one dissecting tool through at least one of said at least two laparoscopic trocars
 f. dissecting in the patient at least one organ selected from the group consisting of: a) the urethra, b) the neck of the urinary bladder c) fibrotic tissue surrounding said organs and d) the muscles surrounding said organs,
 g. implanting at least one powered restriction device in a position that enables it to decrease the cross-sectional area of a) the urethra, b) the neck of the urinary bladder c) fibrotic tissue surrounding said organs and d) the muscles surrounding said organs in order to at least decrease the movement of urine through said passageway.

The additional method according to the first or second preferred method, comprising the additional step of;
 entering the retroperitoneal space from the vaginal opening,
 placing said device in the retroperitoneal cavity,
 fixating said device by the a tunnel created in the fibrotic tissue in said space.

The additional method according to the first or second preferred method, comprising the additional step of;
  entering the fibrotic tissue surrounding the urinary channel from the vaginal opening,
  placing said device in a tunnel of said fibrotic tissue,
  fixating said device by said tunnel.
Further the method, comprising the additional step of;
  placing an energy receiver for receiving wireless energy subcutaneously just above the symphysis bone
  placing an electrical wire between the energy receiver and the device using said vaginal opening as an intermediate passage or using a instrument therefore through said vaginal opening,
  tunnelating the wire subcutaneously from the energy receiver to the device.
Further the method, comprising the additional step of;
  placing an energy receiver for receiving wireless energy subcutaneously just above the symphysis bone
  placing a pump and reservoir above the symphysis bone preferable in the abdominal cavity,
  tunnelating a hydraulic tube subcutaneously from the pump to the device using said vaginal opening as an intermediate passage or using a instrument therefore in said opening.
In yet another embodiment the method, comprising the additional step of;
  introducing a camera through said vaginal opening.
In yet another embodiment the method, comprising the additional step of;
  when introducing a camera through said vaginal opening, using said camera to go around the urinary passageway and
  attaching said device to said camera to thereby,
  passing said device around the urinary passageway using said camera.

The method and the step of implanting a restriction device may include the implantation of a powered restriction device. Preferably it includes the additional step of adjusting said restriction device manually non-invasively.

Preferably the method includes the additional step of implanting an energy receiver in the patient. The energy receiver is preferably implanted subcutaneously, in the pelvic region or the abdomen or in the muscles, legs, or bone surrounding tissue.

The method may include that the energy receiver comprises a motor or a pump that is able to use wireless energy directly and transfer it to kinetic energy.

The method may also include the alternative that the energy receiver comprises an energy transforming device, which may be used for powering a motor or pump directly during energy transfer or indirect through a rechargeable battery, charged by the energy transforming device.

By accessing the urethra and/or the neck of the urinary bladder though an incision in the vagina, patient trauma and discomfort can be kept to a minimum. This will shorten recovery time.

Examples of the restriction device includes but are not limited to U.S. Pat. No. 7,367,938 and EP 1 255 511.

The method comprises steps normally carried out before, under and after surgery such as, but not limited to:
  preparing the patient for surgery, sedating the patient, monitoring sedation and waking up the patient.

In one embodiment, the method comprises a laparoscopical method. In one embodiment the surgical site is accessed after said surgical site has been insufflated with a gas. In one embodiment at least one trocar is used. In one embodiment at least two trocars are used. In one embodiment at least one trocar with a diameter from 5 to 12 mm is used. In one embodiment at least one laparoscopic trocar is inserted through the vaginal wall of the patient, and dissection is performed using at least one dissecting tool, which dissecting tool is inserted through at least one laparoscopic trocar.

A laproscopic method in this case is synonym with key hole surgery and do not need to be performed through the abdominal cavity.

In one embodiment the method comprises the steps of: A) inserting a tube or needle into the body of the patient, B) using said tube or needle to insufflate a site of the body of the patient with a gas, C) inserting at least two laparoscopic trocars into said site, D) inserting at least one camera trough at least one laparoscopic trocar, and E) inserting at least one dissecting tool through at least one laparoscopic trocar, In one embodiment the method comprising the additional step of fixating said restriction device. In one embodiment the method comprising the additional step of fixating said restriction device in the adjacent tissue.

In one embodiment the method comprises the additional step of suturing in layers.

In one embodiment the method comprises restriction is carried out at several different parts of the urethra and/or the neck of the urinary bladder.

In one embodiment the method comprises the additional step of stimulating contraction in at least one of a) the urethra, b) the neck of the urinary bladder or c) the muscles surrounding said organs; by using electricity.

In one embodiment the method comprises the additional step of stimulating more than one location on the restriction device.

In one embodiment the method comprises the step of using cytoscopic observation of the patient. In one embodiment the method comprises the additional step of using a cytoscopic method for placing a sensor in the patient.

In one embodiment the method comprises the additional step of using a cytoscopic method for calibrating the restriction device. In one embodiment the method comprises the additional step of measuring a parameter selected from the group consisting of: an electrical parameter, pressure, volume, diameter, stretching, elongation, extension, movement, elasticity, muscle contraction, temperature, flow and nerve impulse.

Additionally the method according to anyone of the preceding paragraphs, comprising a system for implantation of said restriction device, wherein said system comprising a introductionary hose being hollow and having at least partially a conical shape, adapted to hold said device inside the hollow space to compact the device and make it smaller and conical at the first introductionary end to ease the introduction of the device, wherein the method comprises;
  mounting the restriction device inside said introductionary hose,
  introducing said restriction device around the urethra or the neck of the urine bladder by using said introductionary hose,
  releasing said restriction device from said introductionary hose, and
  withdrawing said hose from the device.

Furthermore, wherein said hose comprising a holding part, adapted to allow an instrument to hold said hose at the first introductionary end to ease the introduction of the device, wherein the method step of introducing said restriction device by using said introductionary hose comprises;
  inserting said instrument via vagina around the urethra or the neck of the urine bladder, attaching said holding part of said introductionary hose to said instrument, and introducing said hose around the urethra or the neck of the urine bladder.

In one embodiment, the restriction device is adjustable in order to allow flow of urine when the patient needs to urinate, and then closing the restriction device in order to stop the flow of urine. In one embodiment, the device is adjusted manually. In one embodiment the device is adjusted non-manually. Normally, the patient will herself determine when the manual adjustment will be used. In an alternative embodiment the device is adjusted automatically. Automatic release is in one embodiment and is only used in emergency situations, such as preventing rupture of the bladder if the pressure becomes too high. That could occur, for example, if the patient loses consciousness.

In one embodiment the restriction device is adjusted from outside the body of the patient, for example by a remote control that is conveniently handled by the patient. In one embodiment the patient uses an implanted switch to control the restriction device. This is useful in case the remote control is lost or breaks down. Preferably the switch is implanted subcutaneously at a convenient location, which in one embodiment is a site which is placed at a distance from the restriction device.

In one embodiment the method comprises the additional step of placing in the body of the patient at least one sensor that measures at least one physiological parameter of the patient. Examples of parameters include, but is not limited to: pressure, volume, diameter, stretching, elongation, extension, movement, elasticity, muscle contraction, temperature and nerve impulse. In one embodiment said sensor is adapted to sending an alarm signal to the patient.

In one embodiment, the method comprises implanting an implantable control device in the patient. The control device is a) adapted to control the energy source, b) adapted to be operated by remote control, and c) adapted to control the restriction device.

The method according to any of the embodiments could be adapted to comprise implanting at least one switch in the patient for manually and non-invasively controlling the restriction device. The energized system enables an operation device to operate the restriction device.

The method could, according to one embodiment, further comprise implanting a hydraulic device having an implantable hydraulic reservoir, which could be hydraulically connected to the restriction device. The restriction device could be adapted to be non-invasively regulated by manually pressing the hydraulic reservoir.

According to another embodiment, the method could further comprise using a wireless remote control for non-invasively controlling the restriction device. The wireless remote control could comprise at least one external signal transmitter and/or receiver, further comprising an internal signal receiver and/or transmitter implantable in the patient for receiving signals transmitted by the external signal transmitter or transmitting signals to the external signal receiver. The wireless remote control could further be adapted to transmit at least one wireless control signal for controlling the restriction device. The wireless control signal could comprise a frequency, amplitude, or phase modulated signal or a combination thereof. The wireless remote control could further be adapted to transmit an electromagnetic carrier wave signal for carrying the control signal.

According to another embodiment the method could comprise using a wireless energy-transmission device for non-invasively energizing the implantable energy consuming components of the restriction device with wireless energy. The wireless energy could comprise a wave signal, selected from the following: a sound wave signal, an ultra-sound wave signal, an electromagnetic wave signal, an infrared light signal, a visible light signal, an ultra violet light signal, a laser light signal, a micro wave signal, a radio wave signal, an x-ray radiation signal, gamma radiation signal, an electric field, a magnetic field, a combined electric and magnetic field.

A control signal could comprise an electric field, a magnetic field, a combined electric and magnetic field. The signal could comprise an analogue signal, a digital signal, or a combination of an analogue and digital signal. For powering the energy consuming components of the restriction device, the implantable restriction device could comprise or be connected to an implantable internal energy source. According to another embodiment the method comprises an external energy source for transferring energy in a wireless mode, wherein the internal energy source is chargeable by the energy transferred in the wireless mode.

According to a further embodiment the method could further comprise implanting a sensor or a measuring device sensing or measuring a functional parameter correlated to the transfer of energy for charging the internal energy source, and a feedback device for sending feedback information from inside the patient's body to the outside thereof, the feedback information could be related to the functional parameter sensed by the sensor or measured by the measuring device.

According to yet another embodiment, the method could further comprise using a feedback device for sending feedback information from inside the patient's body to the outside thereof, the feedback information being related to at least one of a physical parameter of the patient and a functional parameter related to the restriction device.

The method could, according to one embodiment, further comprise implanting a sensor and/or a measuring device and an implantable internal control unit for controlling the restriction device in response to information being related to at least one of a physical parameter of the patient sensed by the sensor or measured by the measuring device and a functional parameter related to the restriction device sensed by the sensor or measured by the measuring device. The physical parameter could according to one embodiment be a pressure or a motility movement.

The method could, according to one embodiment, comprise using an external data communicator and an implantable internal data communicator communicating with the external data communicator, the internal communicator feeds data related to the restriction device or the patient to the external data communicator and/or the external data communicator feeds data to the internal data communicator.

The method according to any of the embodiments herein could further comprise using a motor or a pump for operating the restriction device, or a hydraulic operation device for operating the restriction device. The operation device could comprise a servo designed to decrease the force needed for the operation device to operate the restriction device instead the operation device acting a longer way, increasing the time for a determined action.

According to one embodiment the method could further comprise using an operation device for operating the restriction device and components connected thereto. The wireless energy could be used in its wireless state to directly power the operation device to create kinetic energy for the operation of the restriction device, as the wireless energy is being transmitted by the energy-transmission device. The method could also comprise using an energy-transforming device for transforming the wireless energy transmitted by the energy-transmission device from a first form into a second form energy.

The energy-transforming device could be adapted to directly power implantable energy consuming components of the restriction device with the second form energy, as the energy-transforming device transforms the first form energy transmitted by the energy-transmission device into the second form energy. The second form energy could comprise at least one of a direct current, pulsating direct current and an alternating current. The energy of the first or second, form could comprise at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

For protecting the restriction device and the components connected thereto, the method could further comprise implanting an implantable electrical component including at least one voltage level guard and/or at least one constant current guard. A control device could be arranged to control the transmission of wireless energy from the energy-transmission device, and an implantable internal energy receiver for receiving the transmitted wireless energy, the internal energy receiver could be connected to implantable energy consuming components of the restriction device for directly or indirectly supplying received energy thereto, the method could further comprise a determination device adapted to determine an energy balance between the energy received by the internal energy receiver and the energy used for the implantable energy consuming components of the restriction device, the control device could be adapted to control the transmission of wireless energy from the external energy-transmission device, based on the energy balance determined by the determination device.

The determination device could be adapted to detect a change in the energy balance, the control device could be adapted to control the transmission of wireless energy based on the detected energy balance change. The determination device could in turn be adapted to detect a difference between energy received by the internal energy receiver and energy used for the implantable energy consuming components of the restriction device, and the control device could be adapted to control the transmission of wireless energy based on the detected energy difference.

The energy-transmission device could comprise a coil placed externally to the human body, which in turn could further comprise an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power. The electric circuit could be adapted to deliver the electrical pulses to remain unchanged except varying the first and/or second time intervals.

The method could according to one embodiment comprise using an electric circuit having a time constant which is adapted to vary the first and second time intervals only in the range of the first time constant, so that when the lengths of the first and/or second time intervals are varied, the transmitted power over the coil is varied.

The implantable internal energy receiver for receiving wireless energy could comprise an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the method further comprises using a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

The method could also comprise implanting and internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the method further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In the embodiments in which the method comprises using an external second coil, the external second coil could be adapted to be moved in relation to the internal first coil to establish the optimal placement of the second coil, in which the coupling factor is maximized. The external second coil could also be adapted to calibrate the amount of transferred energy to achieve the feedback information in the determination device, before the coupling factor is maximized.

In one embodiment the method comprises the step of implanting in the patient an energy receiver. In one embodiment the energy receiver is implanted subcutaneously. In one embodiment the energy receiver is implanted in the pelvic region.

In one embodiment the energy receiver comprises a motor or a pump that is able to use wireless energy directly. In one embodiment the energy receiver comprises an energy transforming device. In one embodiment the energy transforming device is used for powering a motor or pump directly. In one embodiment the energy transforming device is used for charging an energy storage device.

In one embodiment the restriction device is fixed in the body of the patient. In one embodiment this is done by fixating the restriction device in the adjacent tissue. After fixating, the incisions in the patient are closed by various means. One mean is suturing in layers. If a minimally invasive procedure has been used, the incision may be so small that other means, for example stapling or taping, are used.

The urethra, the neck of the urinary bladder and various sphincters are equipped with muscle tissue that is able to contract and thus control the flow of urine. Dysfunction of this capacity can be one cause of urinary incontinence. However, the capacity of muscle tissue to contract may be partially or completely restored by stimulating the muscle tissue with electricity. In one embodiment the method comprises stimulating contraction of the muscles surrounding the urethra and/or neck of the urinary bladder by using electricity. In one embodiment, the stimulation takes place in more than one location of the restriction device.

Further aspects and embodiments are defined in the appended claims, which are specifically incorporated herein by reference.

Other features and uses of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

BRIEF DESCRIPTION OF THE DRAWINGS

FIGS. 11-25 schematically show various embodiments of the system for wirelessly powering the restriction device and components connected thereto shown in FIG. 10.

DETAILED DESCRIPTION

Before the invention is disclosed and described in detail, it is to be understood that this invention is not limited to particular surgical steps, configurations, method steps, substrates, and materials disclosed herein as such surgical steps, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meaning commonly understood by those of skill in the art to which this invention pertains.

The term "about" as used in connection with a numerical value throughout the description and the claims denotes an interval of accuracy, familiar and acceptable to a person skilled in the art. Said interval is ±10%.

As used herein, the following terms refers to the following:

"consumed energy" refers to energy consumed by a system or a device,

"dissect" refers to cut with precision surrounding tissue as to expose,

"energy balance" refers to the difference between two measurements of energy,

"implanting" refers to: to set or fix in the human body,

"neck of the urinary bladder" refers to the narrowing part of the urinary bladder that tapers off into to the urethra, "received energy" refers to energy received by a system by means of a energy transfer method, "restriction device" refers to a device that is able to restrict or stop the flow trough a tubular organ, "transmitted energy" refers to energy transmitted by means of a energy transfer method, "urethra" refers to the canal that carries urine from the urinary bladder, "urinary incontinence" refers to inability to control discharge of urine.

"restriction device and components connected thereto" includes the restriction device and any operating device, energy receiver, determination device, energy-transforming device, switches and other components connected (wireless or not) to the restriction device whether electrical, mechanical or hydraulical.

"system" refers to the restriction device and components connected thereto includes the restriction device and any operating device, energy receiver, determination device, energy-transforming device, switches and other components connected (wireless or not) to the restriction device whether electrical, mechanical or hydraulical.

Figure 1:
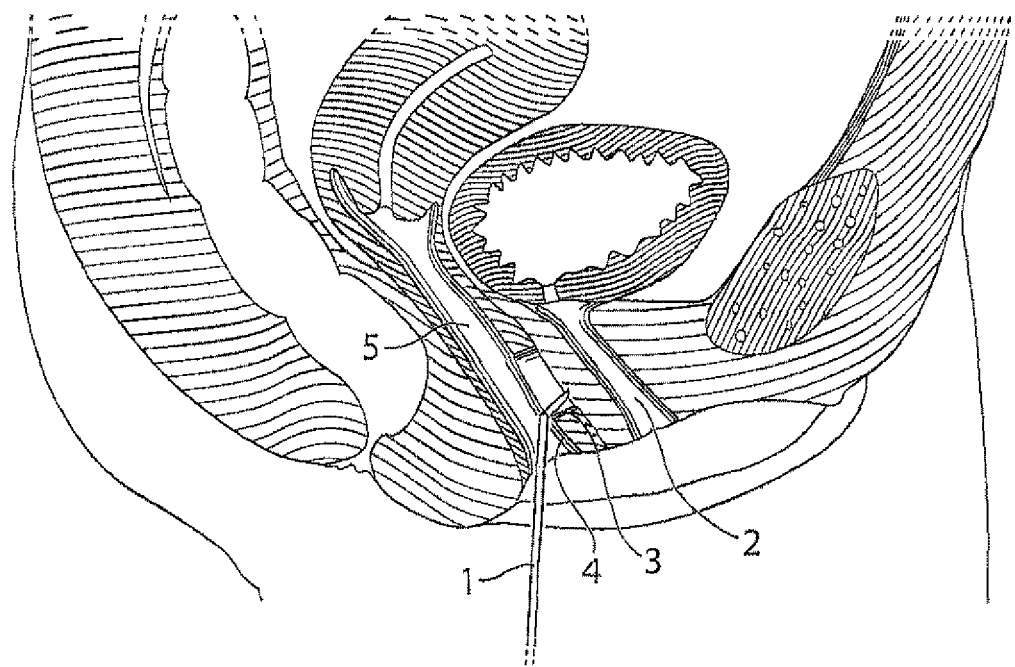
FIGS. 1-3 show how the urethra is accessed through an incision in the vagina and how a restriction device is implanted.

FIG. 1 shows how the surgeon uses a surgical tool 1 to access the urethra 2 through an incision 3 in the wall 4 of the vagina 5 of the patient.

Figure 2A:
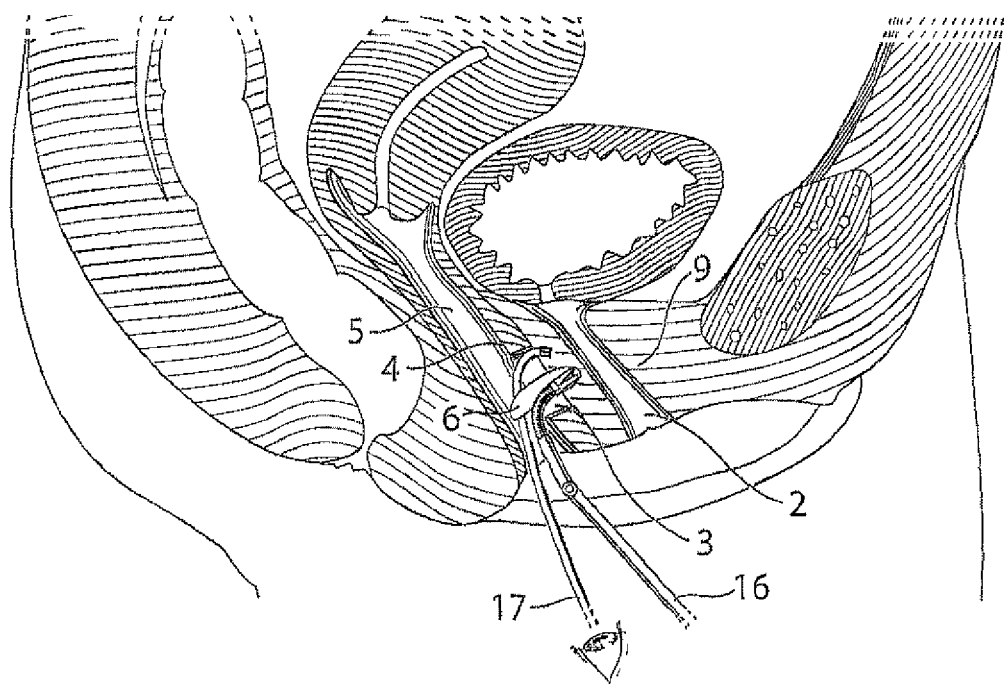

FIG. 2a shows a subsequent step of the method, where a viewing scope 17 has been inserted through the incision 3 in the wall 4 of the vagina 5. The viewing scope allows the surgeon to carry out surgical procedures in a minimally invasive manner. A surgical instrument 16 is used for dissecting the area 9 around the urethra 2 and for the implantation of the restriction device 6.

FIGS. 2b-2e show in detail one method of implanting the restriction device 6, where the urethra 2 is shown non-proportionally large in comparison with the vagina 5. The method is described with reference to the urethra, but a similar method can be used for implanting a restriction device that engages the neck of the urine bladder.

First an incision 3 is made in the wall 4 of the vagina 5 of the patient.

Figure 2B:
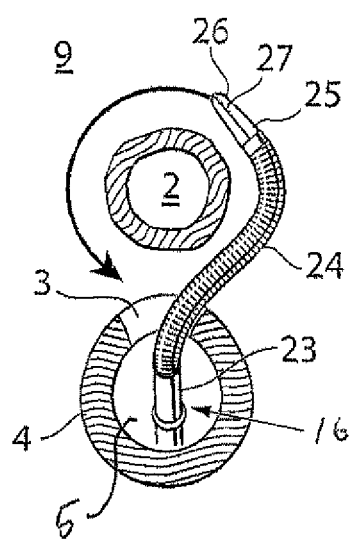
Figure 2C:
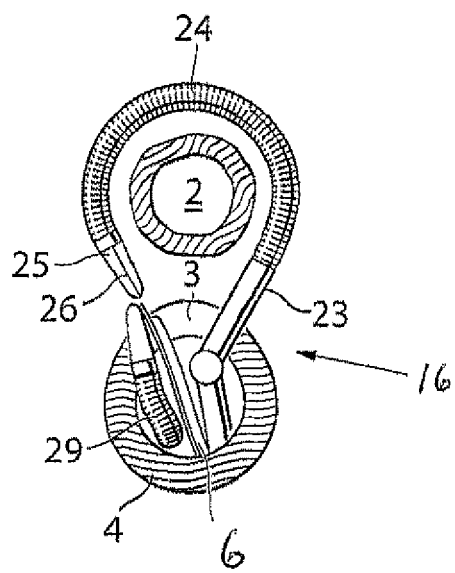

A soft tissue dissector 27 at the end 25 of the flexible tip 24 of the instrument 16 is used to push through the area 9 surrounding the urethra 2 as shown in FIG. 2b. When the flexible tip 24 has reached behind the urethra 2 it is slightly bent so that it can dissect behind the urethra 2. The flexible tip 24 is then slightly bent and moved inwards so that it can reach even further behind the urethra 2 until an attachment structure 26 of the head 25 of the flexible tip 24 protrudes from the other side of the urethra as shown in FIG. 2c. The restriction device 6, which is in an open conformation, is brought into the site of surgery with the means of another instrument 29. The attachment structure 26 of the surgical instrument 16 is then attached to the restriction device 6.

Figure 2D:
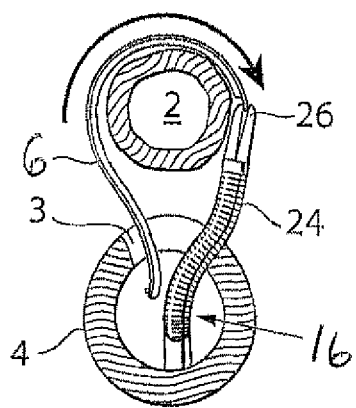
Figure 2E:
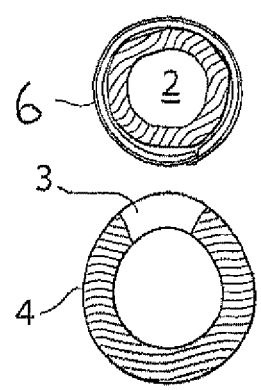

The tip of the surgical instrument 16 is then retracted by performing the reverse movement, thereby pulling the restriction device 6 in place behind the urethra 2 as shown in FIG. 2d. The restriction device 6 is now essentially in place and is detached from the attachment structure 26 of the surgical instrument 16. The restriction device 6 is then closed to form a loop around the urethra 2 as seen in FIG. 2e.

In one embodiment, essentially seen in FIG. 2a, the restriction device 6 is attached to the instrument 16 before the flexible tip 24 is brought in behind the urethra 2. In this embodiment, the device 6 is brought in place as the flexible tip 24 bends around the urethra 2 and the additional instrument 29 is not needed.

In one embodiment the instrument 16 comprises a viewing scope allowing implantation of the device to be carried out with a minimally invasive procedure.

The surgical instrument 16 is in one embodiment used for implanting devices that are associated with the restriction device, such as a control device for controlling the adjustment of the restriction device, and devices for powering the device and for storing energy. Also, in one embodiment, switches sensors and leads are implanted. In one embodiment, more than one restriction device is implanted.

The restriction device (6) may in FIG. 2 additionally be viewed as mounted inside an introductionary hose. Additionally the method according to anyone of the preceding paragraphs, comprising a system for implantation of said restriction device, wherein said system comprising a introductionary hose being hollow and having at least partially a conical shape, adapted to hold said device inside the hollow space (6) to compact the device and make it smaller and conical at the first introductionary end to ease the introduction of the device, wherein the method comprises;

mounting the restriction device inside said introductionary hose,
introducing said restriction device around the urethra or the neck of the urine bladder, by using said introductionary hose,
releasing said restriction device from said introductionary hose, and
withdrawing said hose from the device.

Furthermore, wherein said hose comprising a holding part, adapted to allow an instrument to hold said hose at the first introductionary end to ease the introduction of the device, wherein the method step of introducing said restriction device by using said introductionary hose comprises;

inserting said instrument via vagina around the urethra or the neck of the urine bladder,
attaching said holding part of said introductionary hose to said instrument, and
introducing said hose around the urethra or the neck of the urine bladder.

Figure 3:
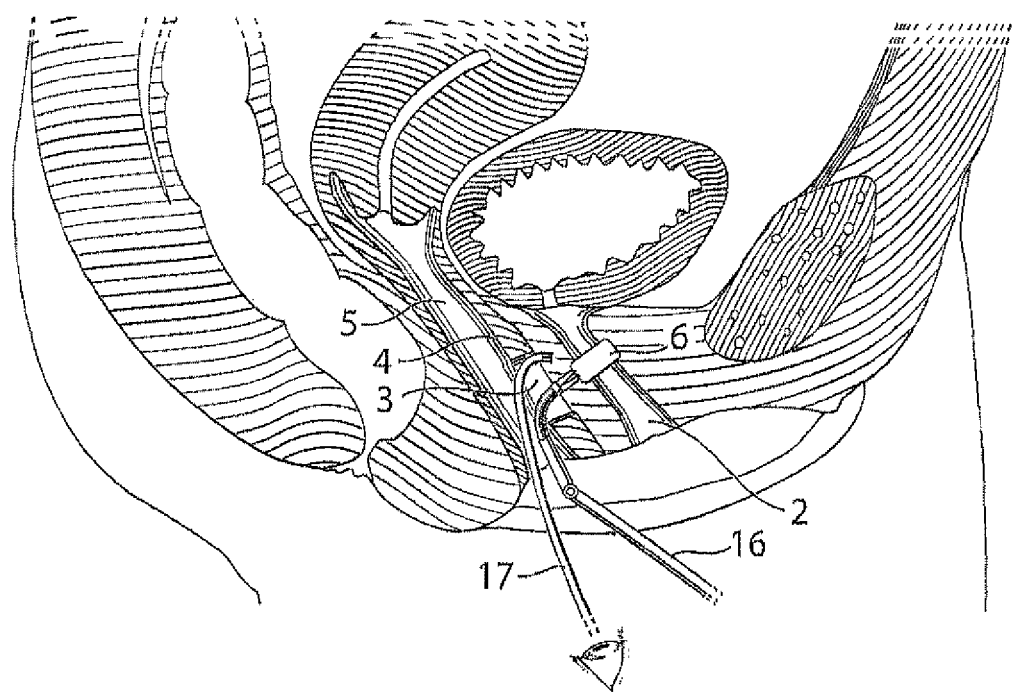

FIG. 3 shows an even later step in the surgical procedure. The restriction device 6 is now in place engaging the urethra 2 and the surgical instrument 16 is being retracted. Other devices that are to be connected to the restriction device such a control device, a switch, a energy source and a sensor can be implanted and connected to the restriction device during the same procedure, if desired. After implantation, the incision 3 in the wall 4 of the vagina 5 is sutured.

In one embodiment of the method, a laparoscopic surgical procedure is used. Laparoscopic surgical procedures involve percutaneously accessing an internal surgical site with small-diameter access tubes (typically 5 to 12 mm diameter), usually referred to as laparoscopic trocars, which penetrate the skin and permit access to the surgical site. A viewing scope is introduced through at least one laparoscopic trocar and the surgeon performs surgery using instruments inserted through other appropriately placed laparoscopic trocar(s) while viewing the operative site on for instance a video monitor connected to the viewing scope. The surgeon is thus able to perform a wide variety of surgical procedures requiring only a few 5 to 12 mm punctures at the surgical site, Consequently, patient trauma and recovery time are greatly reduced. Laparoscopic procedures may involve the insufflation of the surgical site with gas in order to create sufficient operating space to perform a desired procedure. Usually more than one trocar is used. In one embodiment at least one trocar is used for inserting a dissecting tool and dissecting the area around the urethra or the neck of the urinary bladder.

Figure 4:
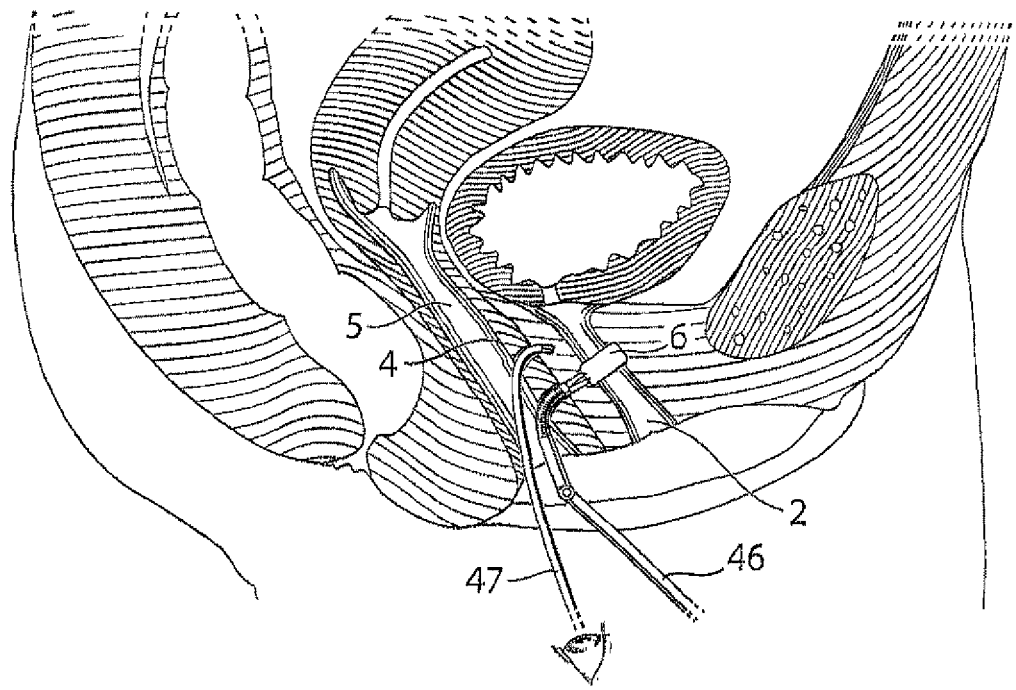
FIG. 4 shows an embodiment where a laparoscopical surgical method is used.

FIG. 4 show and embodiment where a laparoscopic method is used. Trocars are inserted in the vagina and trough the wall 4 of the vagina 5 of the patient in order to access the urethra 2. One trocar 46 is used for placing a restriction device 6 on the urethra 2 and one trocar 47 is used for inserting a viewing scope or a camera for observing the urethra 2 from the outside.

Cytoscopy is a technology that involves inserting a probe with a camera in the urethra of the patient. This enables the operator to visually inspect the urethra and/or the urinary bladder. In one embodiment the surgical procedure is combined with cystoscopy. This enables the surgeon to observe the lumen of the urethra while surgery is being performed. This can be used to, for example, se how much the urethra contracts when the restriction device is engaged and allows for the verification of the correct positioning of the restriction device.

Figure 5:
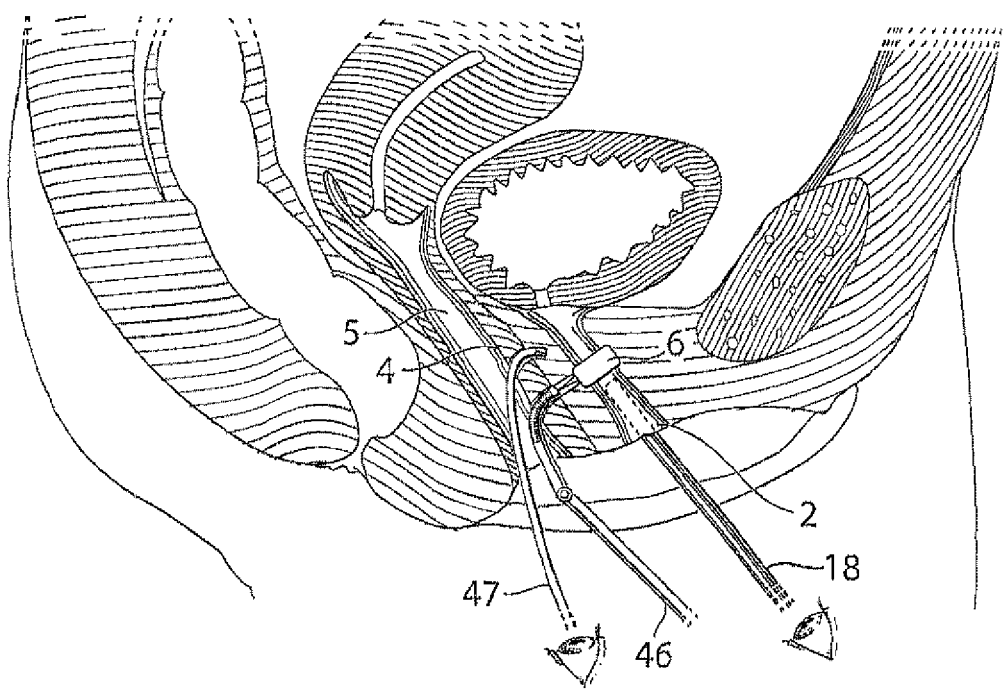
FIG. 5 shows how the method for surgery is combined with a cytoscopic method.

FIG. 5 shows how a cytoscope 18 is inserted through the urethra 2 enabling the surgeon to observe the interior of the urethra 2, while using trocars 46, 47 for placing a restriction device 6 on the urethra 2 and for observing the urethra 2 from the outside. Furthermore, in one embodiment, cystoscopy is used for placing a sensor in the patient. In one embodiment, the sensor measures an electrical parameter. In an alternative embodiment the senor measures one parameter from the group consisting of pressure, volume, diameter, stretching, elongation, extension, movement, elasticity, muscle contraction, temperature and flow and nerve impulse. In one embodiment output from the sensor is used for calibrating the restriction device.

Figure 6:
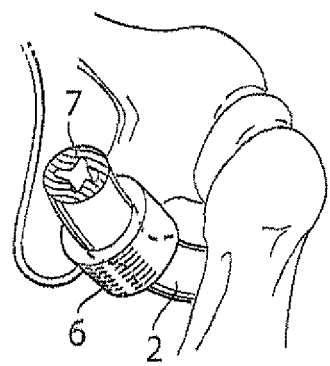
FIG. 6 show how the restriction device is engaging the urethra.

FIG. 6 shows the restriction device 6 implanted and engaging the urethra 2 and being able to decrease the cross sectional area of the urine passageway 7 in order to stop or decrease the flow of urine.

Figure 7:
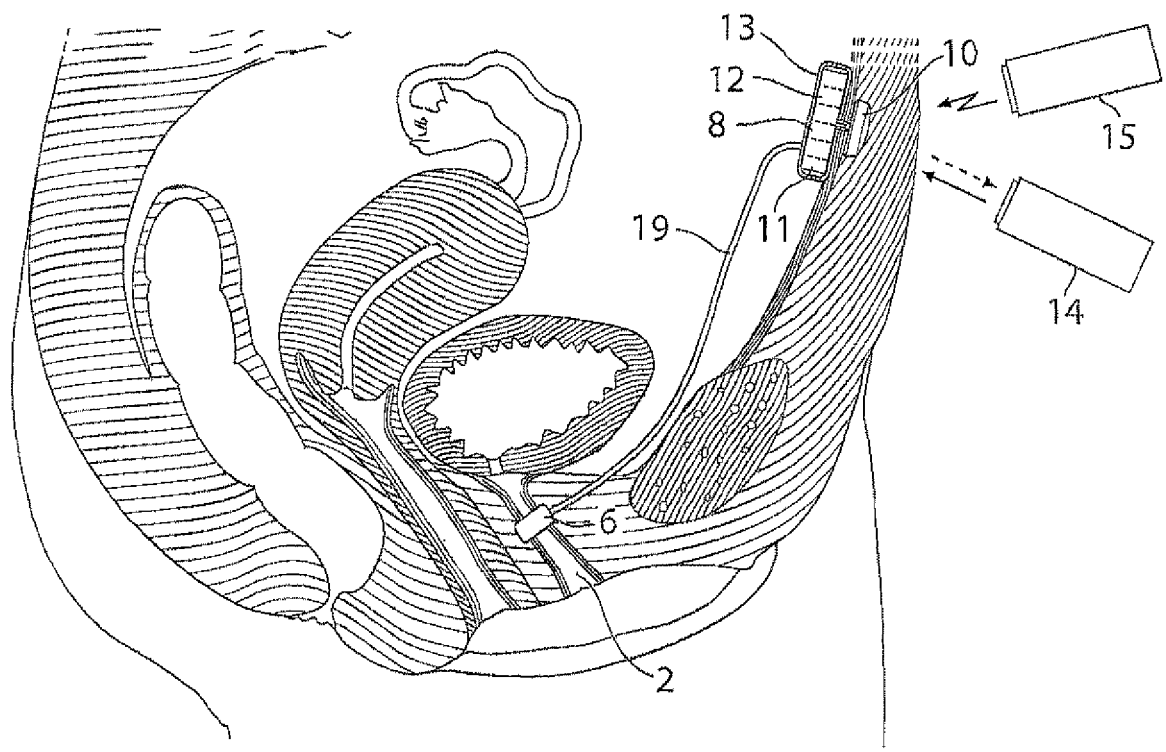
FIG. 7 shows how the restriction device is combined with a control device, a remote control an external energy source.

FIG. 7 shows the restriction device 6 implanted and engaging the urethra 2. It is adjustable and connected to the control device 8 by a power- and control cord 19. The control device comprises a subcutaneous switch 10, a receiver for wireless energy 11, a battery 12, a receiver 13 for a remote control 14. Wireless energy is transmitted by a transmitter 15.

Figure 8:
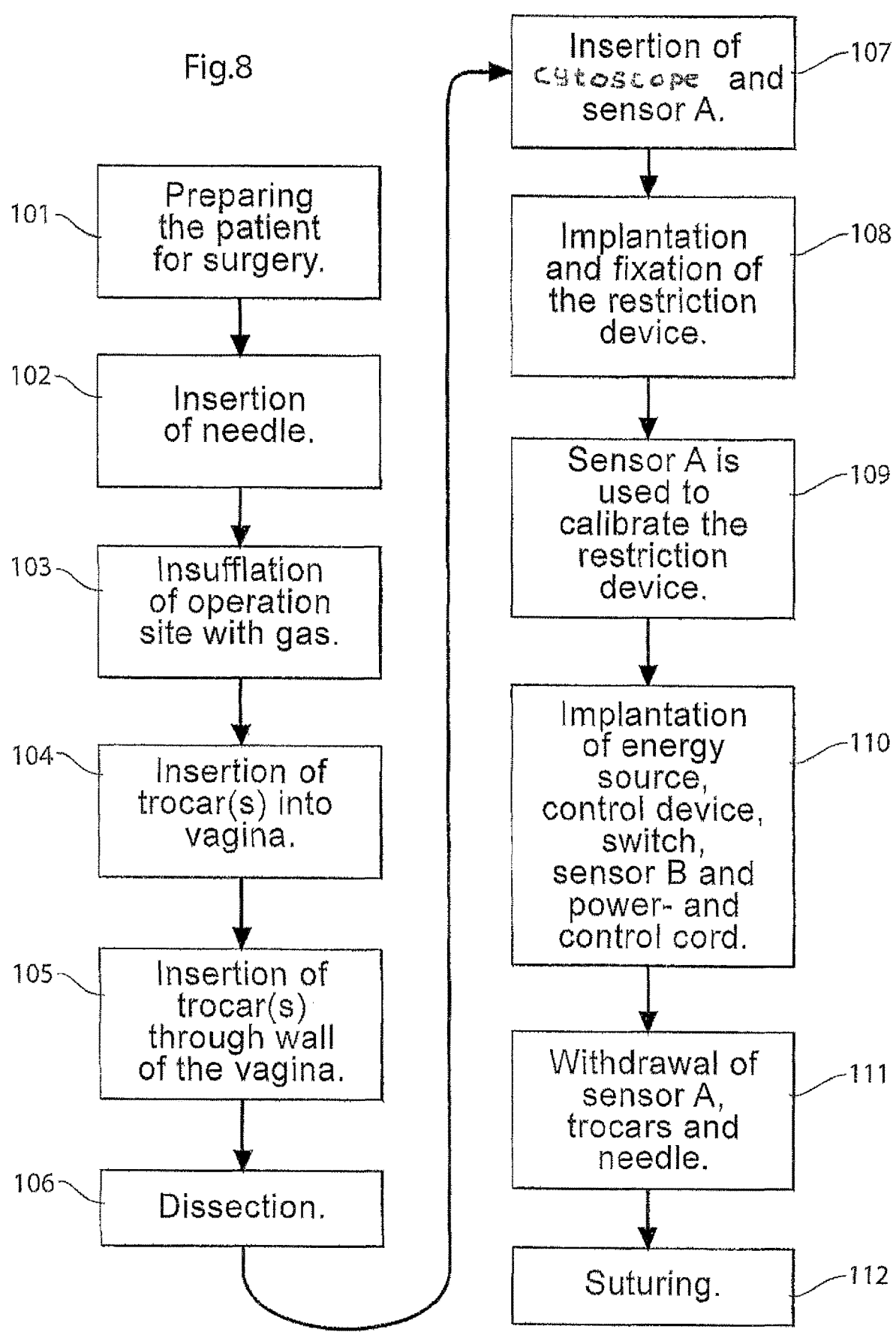
FIG. 8 is a flow chart that describes a method for treatment of a female patient suffering from urinary incontinence involving a laparoscopic surgery method.

FIG. 8 is a flow chart that shows one embodiment that includes several of the steps of the disclosed method where a minimally invasive method for surgery is used. In other embodiments, one or more steps may be omitted or performed in a different order. In step 101, the patient is prepared for surgery in a manner that is known to a person skilled in the art. Preferably, the method is performed on the patient in the supine position. In step 102 a needle is introduced into the site of operation. In step 103, the site of operation is insufflated with a gas so that the site of operation is expanded. Step 104 is the insertion into the vagina of trocars. At least one trocar is used for viewing the operation site and at least one trocar is used for performing various surgical step. The trocars are then in step 105 inserted through the wall of the vagina. Preferably, the trocars are inserted through the anterior wall of the vagina. The tips of the trocars are brought up to the site of surgery which is the urethra and/or the neck of the urine bladder. Step 106 is dissection of the urethra and/or neck of urine bladder. A cytoscope is then, in step 107, inserted through the urethra. In one embodiment a sensor (sensor A in the figure) is introduced by using the cytoscope. The cytoscope is used to observe the urethra from the inside during step 108, which is the implantation of the restriction device so that it engages the urethra and/or the neck of the urine bladder. By viewing the urethra from the inside with the cytoscope, the surgeon can make sure that the restriction device engages the urethra and/or neck of urine bladder in a correct manner. The restriction device is also fixated in the surrounding tissue of the patient in step 108. Sensor A is used in step 109 to calibrate the restriction device. Sensor A is then removed from the patient. In step 110, other parts are implanted in the patient, such as, but not limited to, an energy source, control device and a switch. These may be included in the same subcutaneous implant. A control cord, that connects the restriction device to the control device, and sensor B, are also implanted, in one embodiment. Step 111 is the withdrawal of the trocars, the cytoscope and sensor A. In step 112 the incisions are closed by suturing or other means, such as taping, clamping or stapling. In one embodiment, step 109 is omitted. In one embodiment step 107 is omitted. In one embodiment, step 107 is carried out before step 106. In one embodiment, step 110 is carried out before step 109.

Figure 9:
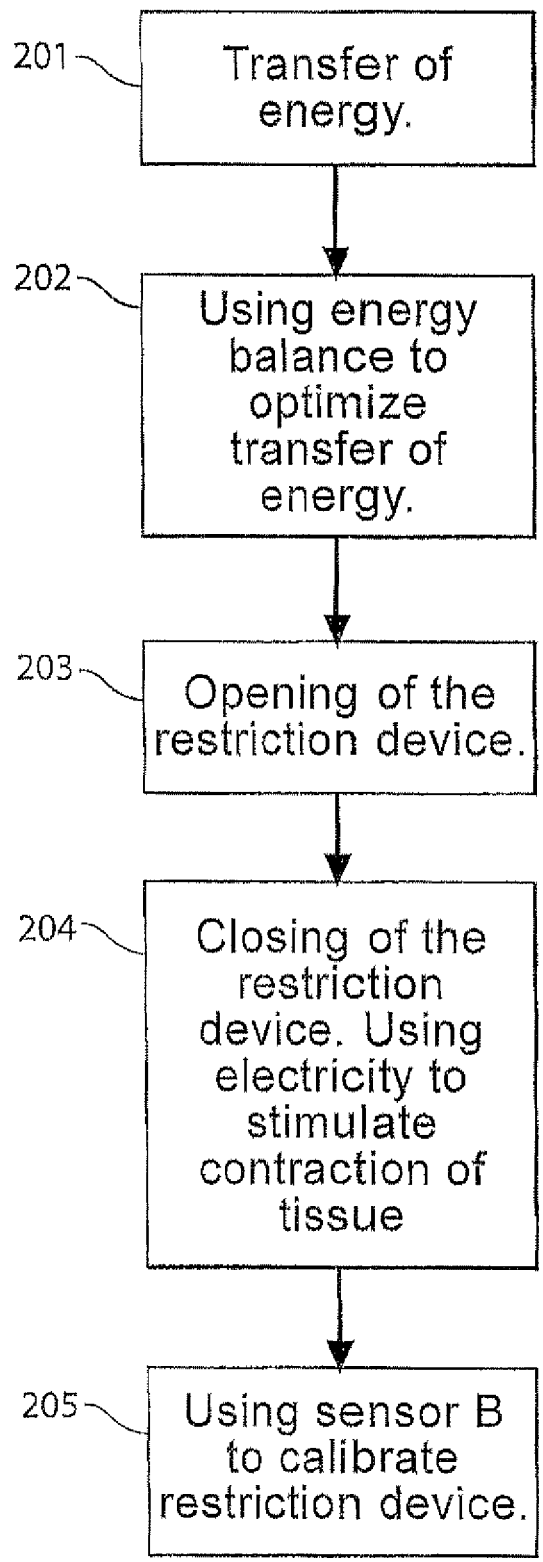
FIG. 9 is a flow chart showing how the method for treating a female patient suffering from urinary incontinence is used postoperatively.

FIG. 9 is a flow chart that shows one embodiment of how the method is used postoperatively, where the implanted parts are used to control the flow of urine in a urine incontinent patient. This is one example of an embodiment only, and one or more steps may be omitted or performed in a different order. In step 201, energy is transferred to the energy source. In step 202, the energy balance is used to optimize the transfer of energy. In step 203, the patient opens the restriction device to allow the flow of urine when the patient needs to urinate. In step 204, the restriction device is closed after the patient has finished urinating. Simultaneously, electricity is used to stimulate contraction of muscles that control the flow of urine. In step 205, the implanted sensor B is used to calibrate the restriction device. In one embodiment step 205 is omitted. In one embodiment, step 205 is carried out before step 203.

Figure 10:
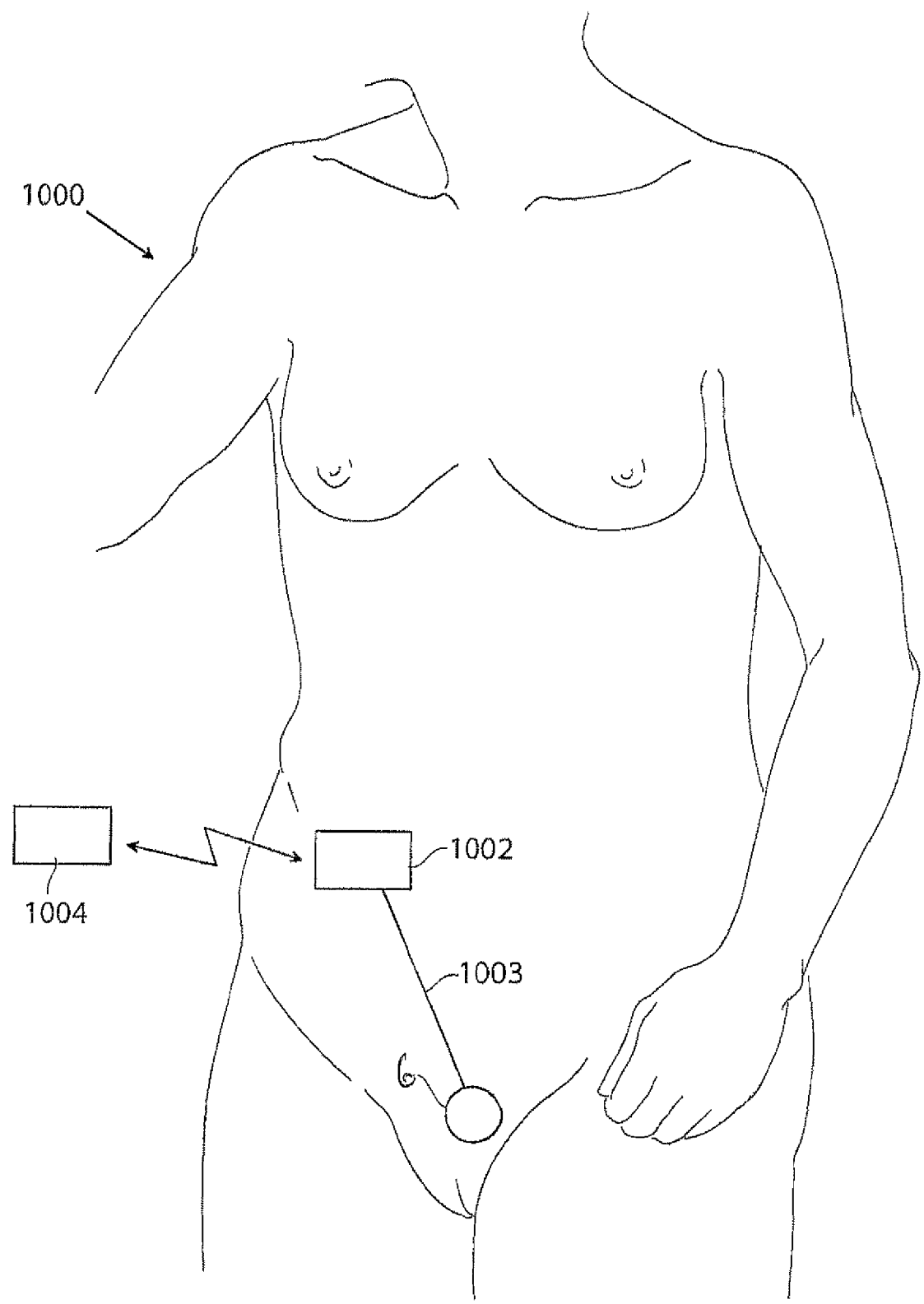
FIG. 10 illustrates an overview of the restriction device with components connected thereto comprising a system.

FIG. 10 illustrates a method for treating urine incontinence in a woman, comprising the implantation of a system 1000 comprising a restriction device 6 of the present invention, in the patient. An implanted energy-transforming device 1002 is adapted to supply energy consuming components of the restriction device 6 with energy via a power supply line 1003. An external energy-transmission device 1004 for non-invasively energizing the restriction device 6 transmits energy by at least one wireless energy signal. The implanted energy-transforming device 1002 transforms energy from the wireless energy signal into electric energy which is supplied via the power supply line 1003.

The implanted energy-transforming device 1002 may also comprise other components, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted restriction device 6 is operable in response to the energy of the second form. The energy-transforming device 1002 may directly power the restriction device 6 with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the restriction device 6 and any components connected thereto, as the wireless energy is being transmitted by the energy-transmission device 1004. Where the system comprises an operation device for operating the restriction device 6, as will be described below, the wireless energy transmitted by the energy-transmission device 1004 may be used to directly power the operation device to create kinetic energy for the operation of the restriction device.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the restriction device 6 comprises electric components that are energized with electrical energy. Other implantable electric components of the system may be at least one voltage level guard or at least one constant current guard connected with the electric components of the restriction device 6.

Optionally, the energy of the first form and the energy of the second form may comprise magnetic energy, kinetic energy, sound energy, chemical energy, radiant energy, electromagnetic energy, photo energy, nuclear energy or thermal energy. Preferably, the energy of the first form and the energy of the second form are non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the restriction device 6. Alternatively, the energy-transmission device is controlled from outside the patient's body to release non-magnetic wireless energy, and the released non-magnetic wireless energy is used for operating the restriction device 6.

The external energy-transmission device 1004 also includes a wireless remote control having an external signal transmitter for transmitting a wireless control signal for non-invasively controlling the restriction device 6. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 11 illustrates the system 1000 of FIG. 10 in the form of a more generalized block diagram showing the restriction device 6, the energy-transforming device 1002 powering the restriction device 6 via power supply line 1003, and the external energy-transmission device 1004, The patient's skin 1005, generally shown by a vertical line, separates the interior of the patient to the right of the line from the exterior to the left of the line.

FIG. 12 shows an embodiment of the invention identical to that of FIG. 11, except that a reversing device in the form of an electric switch 1006 operable for example by polarized energy also is implanted in the patient for reversing the restriction device 6. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the restriction device 6.

FIG. 13 shows an embodiment of the invention identical to that of FIG. 11, except that an operation device 1007 implanted in the patient for operating the restriction device 6 is provided between the implanted energy-transforming device 1002 and the restriction device 6. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 14 shows an embodiment of the invention identical to that of FIG. 11, except that it also comprises an operation device in the form of an assembly 1008 including a motor/pump unit 1009 and a fluid reservoir 1010 is implanted in the patient. In this case the restriction device 6 is hydraulically operated, i.e. hydraulic fluid is pumped by the motor/pump unit 1009 from the fluid reservoir 1010 through a conduit 1011 to the restriction device 6 to operate the restriction device 6, and hydraulic fluid is pumped by the motor/pump unit 1009 back from the restriction device 6 to the fluid reservoir 1010 to return the restriction device 6 to a starting position.

The implanted energy-transforming device 1002 transforms wireless energy into a current, for example a polarized current, for powering the motor/pump unit 1009 via an electric power supply line 1012.

Instead of a hydraulically operated restriction device 6, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 15:
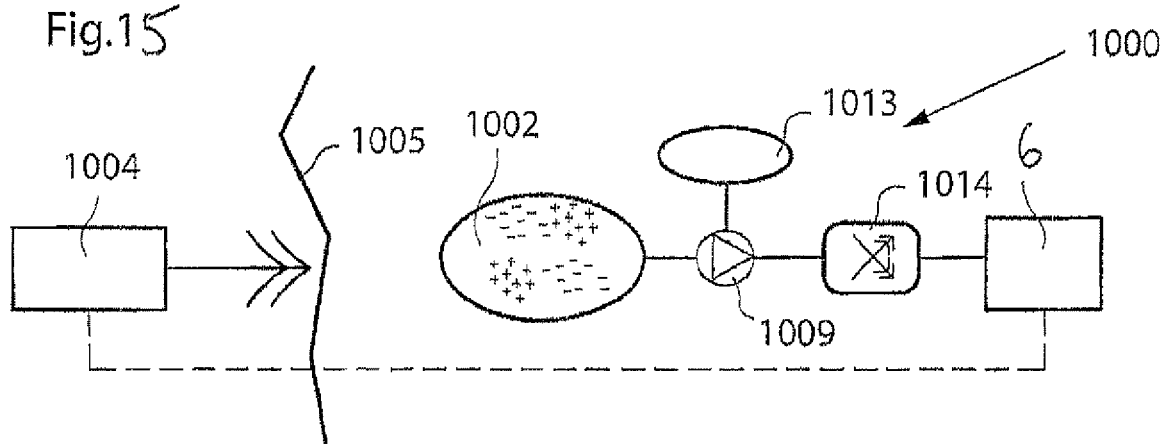

FIG. 15 shows an embodiment of the invention comprising the external energy-transmission device 1004 with its wireless remote control, the restriction device 6, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the restriction device 6. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the restriction device 6 to operate the restriction device 6, and another opposite direction in which the fluid is pumped by the motor/pump unit 1009 back from the restriction device 6 to the hydraulic fluid reservoir 1013 to return the restriction device 6 to a starting position.

Figure 16:
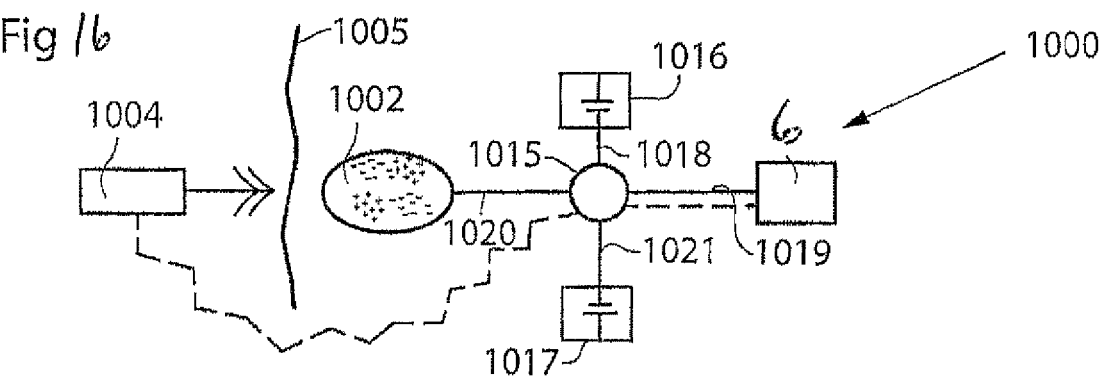

FIG. 16 shows an embodiment of the invention comprising the external energy-transmission device 1004 with its wireless remote control, the restriction device 6, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the restriction device 6. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the restriction device 6.

The internal control unit is preferably programmable from outside the patient's body. In a preferred embodiment, the internal control unit is programmed to regulate the restriction device 6 according to a pre-programmed time-schedule or to input from any sensor sensing any possible physical parameter of the patient or any functional parameter of the system.

In accordance with an alternative, the capacitor 1017 in the embodiment of FIG. 16, 10 may be omitted. In accordance with another alternative, the accumulator 1016 in this embodiment may be omitted.

Figure 17:
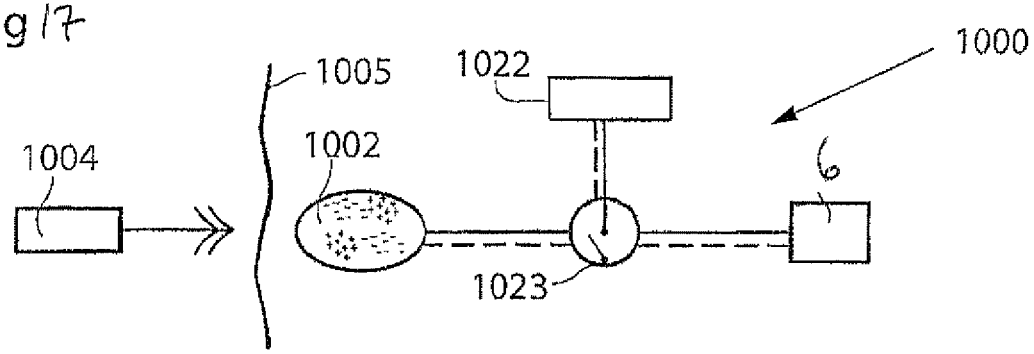

FIG. 17 shows an embodiment of the invention identical to that of FIG. 11, except that a battery 1022 for supplying energy for the operation of the restriction device 6 and an electric switch 1023 for switching the operation of the restriction device 6 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the restriction device 6.

Figure 18:
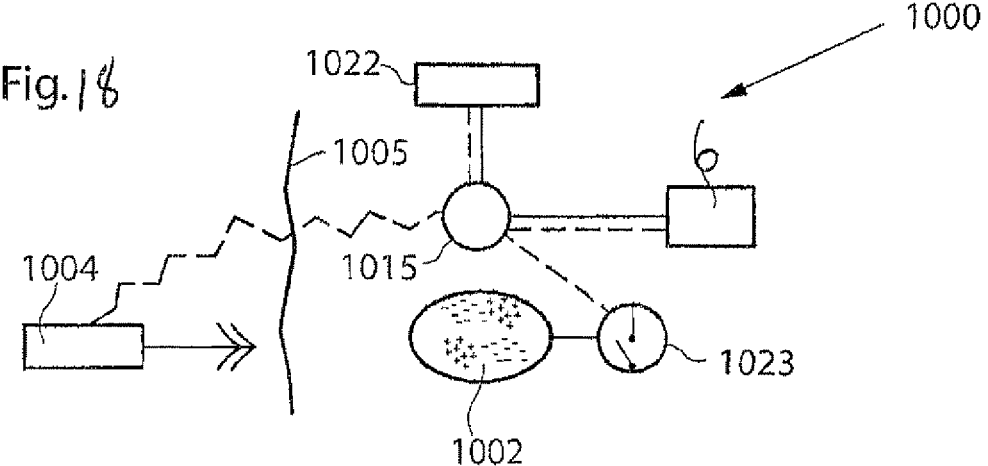

FIG. 18 shows an embodiment of the invention identical to that of FIG. 17, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the restriction device 6.

Figure 19:
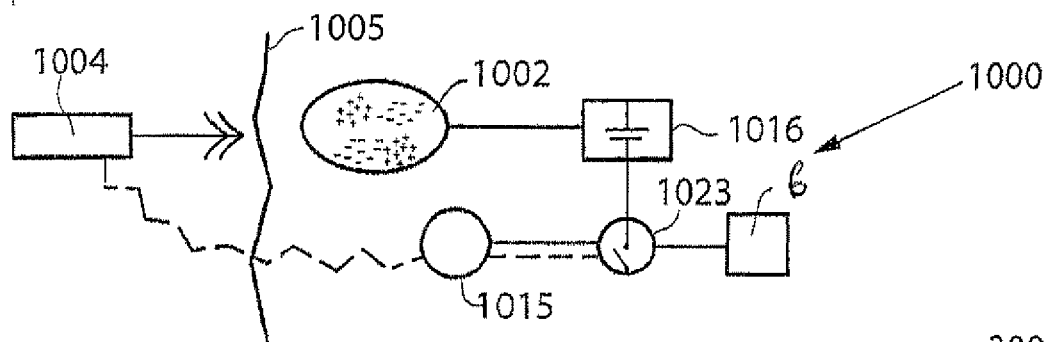

FIG. 19 shows an embodiment of the invention identical to that of FIG. 18, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the restriction device 6. The accumulator may be combined with or replaced by a capacitor.

Figure 20:
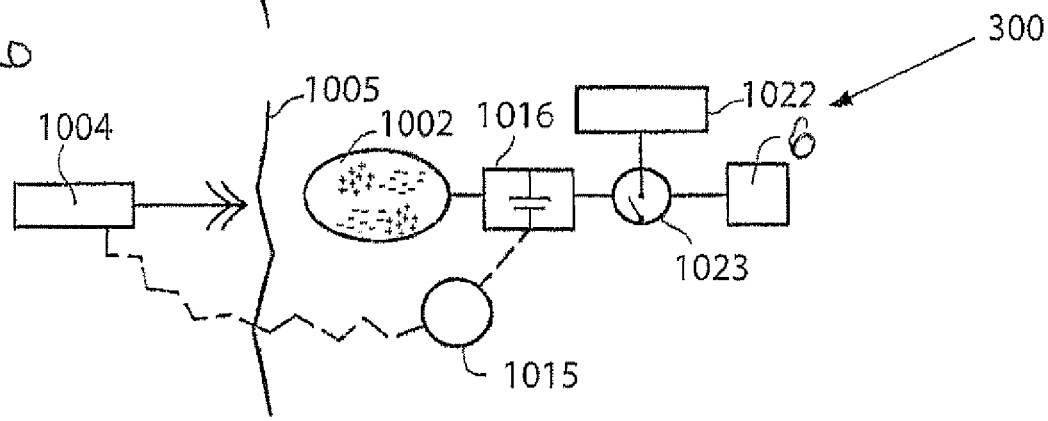

FIG. 20 shows an embodiment of the invention identical to that of FIG. 19, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the restriction device 6.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the restriction device 6.

It should be understood that the switch 1023 and all other switches in this application should be interpreted in its broadest embodiment. This means a transistor, MCU, MCPU, ASIC, FPGA or a CA converter or any other electronic component or circuit that may switch the power on and off. Preferably the switch is controlled from outside the body, or alternatively by an implanted internal control unit.

Figure 21:
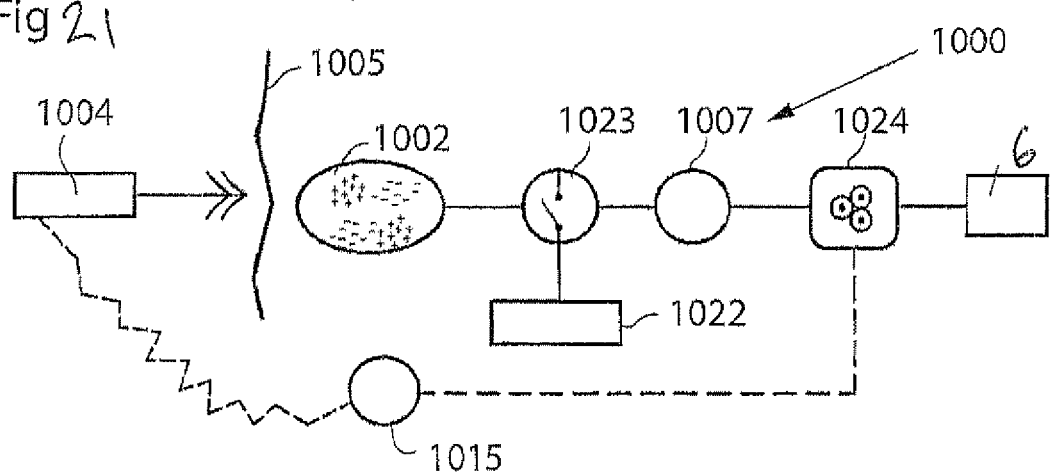

FIG. 21 shows an embodiment of the invention identical to that of FIG. 17, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the restriction device 6 (mechanically operated). Even simpler is to switch the direction of the motor electronically. The gear box interpreted in its broadest embodiment may stand for a servo arrangement saving force for the operation device in favour of longer stroke to act.

Figure 22:
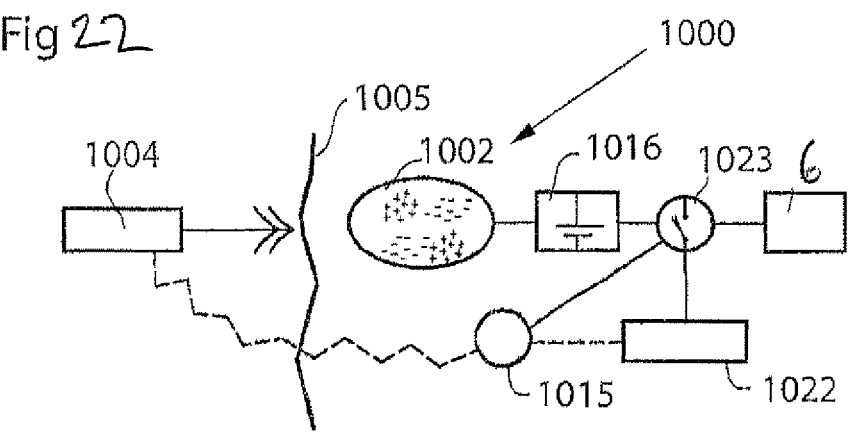

FIG. 22 shows an embodiment of the invention identical to that of FIG. 21 except that the implanted components are interconnected differently. Thus, in this case the internal control unit 1015 is powered by the battery 1022 when the accumulator 1016, suitably a capacitor, activates the electric switch 1023 to switch to an on mode. When the electric switch. 1023 is in its on mode the internal control unit 1015 is permitted to control the battery 1022 to supply, or not supply, energy for the operation of the restriction device 6.

Figure 23:
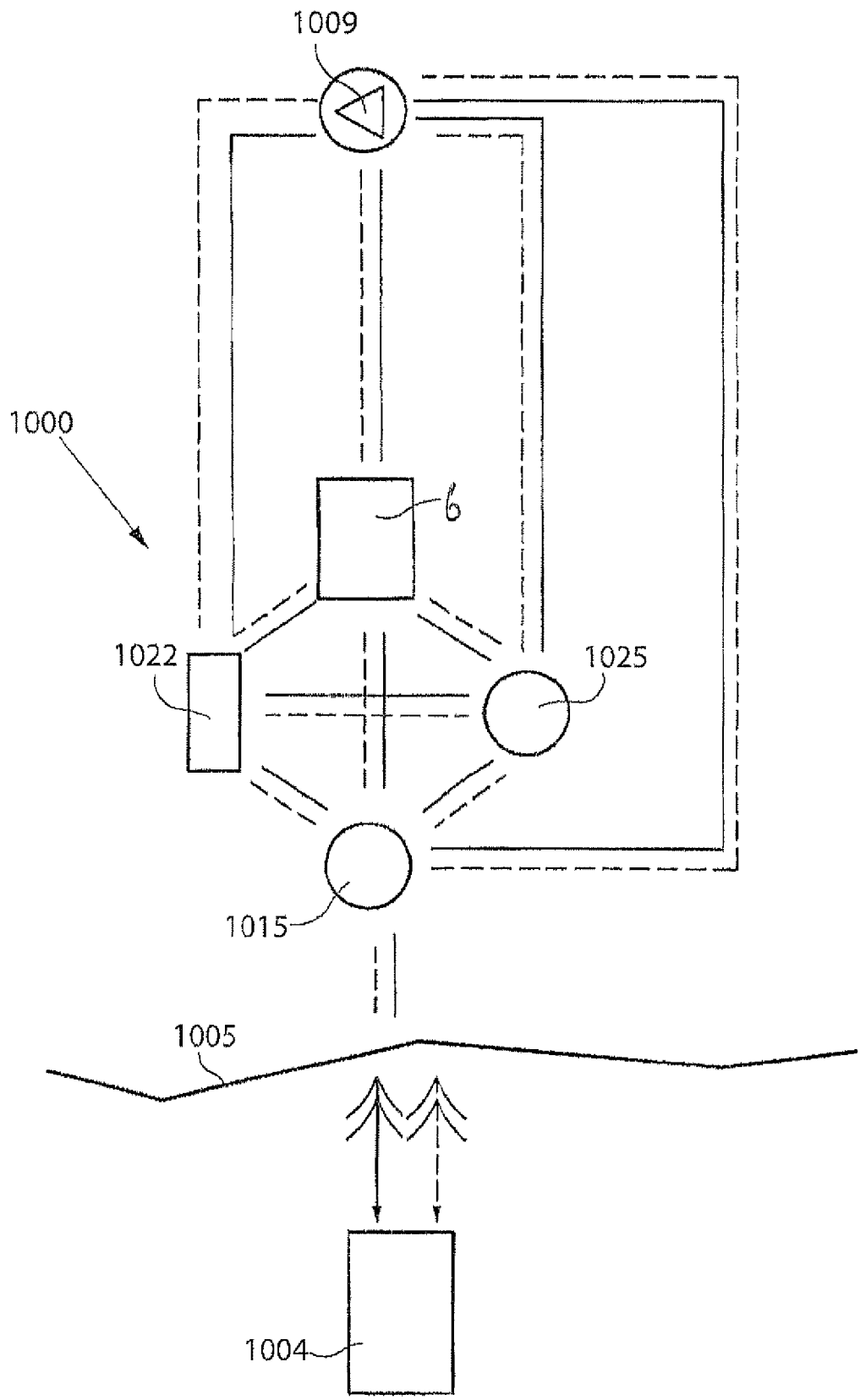

FIG. 23 schematically shows conceivable combinations of implanted components of the restriction device 6 for achieving various communication options. Basically, there are the restriction device 6, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the restriction device 6.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the restriction device 6 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the restriction device 6 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feedback information related to said charging process is sent and the energy supply is changed accordingly.

Figure 24:
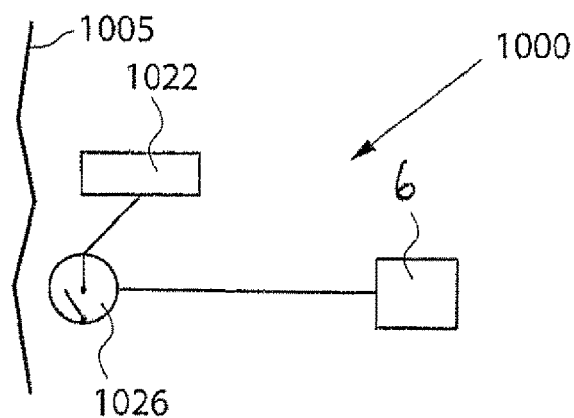

FIG. 24 shows an alternative embodiment wherein the restriction device 6 is regulated from outside the patient's body. The system 1000 comprises a battery 1022 connected to the restriction device 6 via a subcutaneous electric switch 1026. Thus, the regulation of the restriction device 6 is performed non-invasively by manually pressing the subcutaneous switch, whereby the operation of the restriction device 6 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 25:
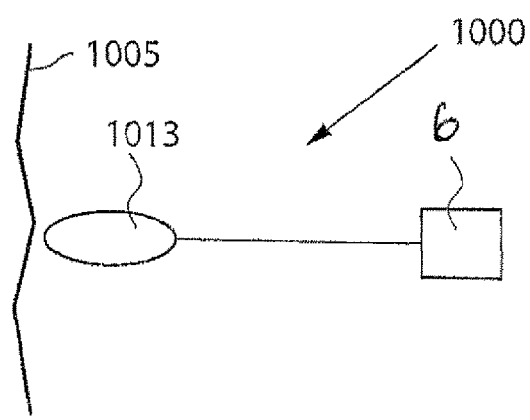

FIG. 25 shows an alternative embodiment, wherein the system 1000 comprises a hydraulic fluid reservoir 1013 hydraulically connected to the restriction device 6. Non-invasive regulation is performed by manually pressing the hydraulic reservoir connected to the restriction device 6. Alternatively, the hydraulic fluid reservoir 1013 is adapted to work with an injection port for the injection of hydraulic fluid, preferably for calibration of hydraulic fluid.

The system may include an external data communicator and an implantable internal data communicator communicating with the external data communicator. The internal communicator feeds data related to the restriction device 6 or the patient to the external data communicator and/or the external data communicator feeds data to the internal data communicator.

Figure 26:
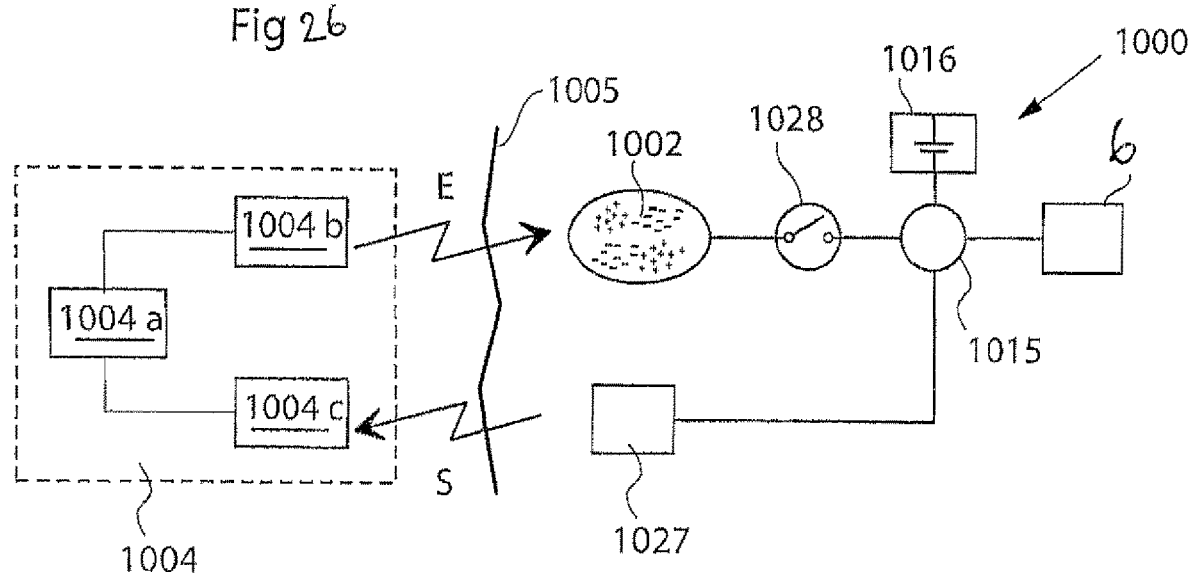
FIG. 26 is a schematic block diagram illustrating an arrangement for supplying an accurate amount of energy used for the operation of the restriction device and components connected thereto shown in FIG. 10.

FIG. 26 schematically illustrates an arrangement of the system that is capable of sending information from inside the patient's body to the outside thereof to give feedback information related to at least one functional parameter of the restriction device 6 or system, or related to a physical parameter of the patient, in order to supply an accurate amount of energy to an implanted internal energy receiver 1002 connected to implanted energy consuming components of the restriction device 6. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the restriction device 6 via a switch 1026. An energy balance is determined between the energy received by the internal energy receiver 1002 and the energy used for the restriction device 6, and the transmission of wireless energy is then controlled based on the determined energy balance. The energy balance thus provides an accurate indication of the correct amount of energy needed, which is sufficient to operate the restriction device 6 properly, but without causing undue temperature rise.

In FIG. 26 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the restriction device 6, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the restriction device 6. The term "energy used" is then understood to include also energy stored by implanted components of the restriction device 6. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the restriction device 6. The internal control unit 1015 may thus be arranged to receive various measurements obtained by suitable sensors or the like, not shown, measuring certain characteristics of the restriction device 6, somehow reflecting the required amount of energy needed for proper operation of the restriction device 6. Moreover, the current condition of the patient may also be detected by means of suitable measuring devices or sensors, in order to provide parameters reflecting the patient's condition. Hence, such characteristics and/or parameters may be related to the current state of the restriction device 6, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the restriction device 6. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the restriction device 6, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the restriction device 6, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements.

Hence, the present solution according to the arrangement of FIG. 26 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the restriction device 6. The restriction device 6 may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the restriction device 6.

The internal signal transmitter 1027 and the external signal receiver 1004c may be implemented as separate units using suitable signal transfer means, such as radio, IR (Infrared) or ultrasonic signals. Alternatively, the internal signal transmitter 1027 and the external signal receiver 1004c may be integrated in the implanted energy-transforming device 1002 and the external energy source 1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 26, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 26 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement results from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 27:
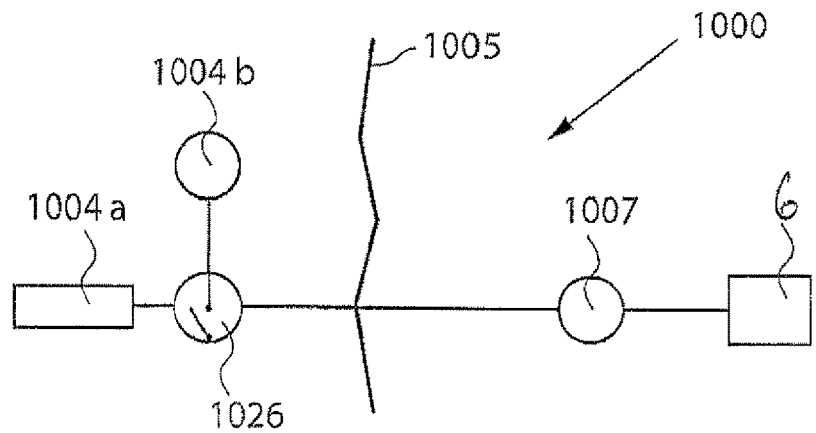
FIG. 27 schematically shows an embodiment of the system, in which the restriction device is operated with wire-bound energy.

With reference to FIG. 27, although wireless transfer of energy for operating the restriction device 6 has been described above to enable non-invasive operation, it will be appreciated that the restriction device 6 can be operated with wire bound energy as well. Such an example is shown in FIG. 27, wherein an external switch 1026 is interconnected between the external energy source 1004a and an operation device, such as an electric motor 1007 operating the restriction device 6. An external control unit 1004b controls the operation of the external switch 1026 to effect proper operation of the restriction device 6.

Figure 28:
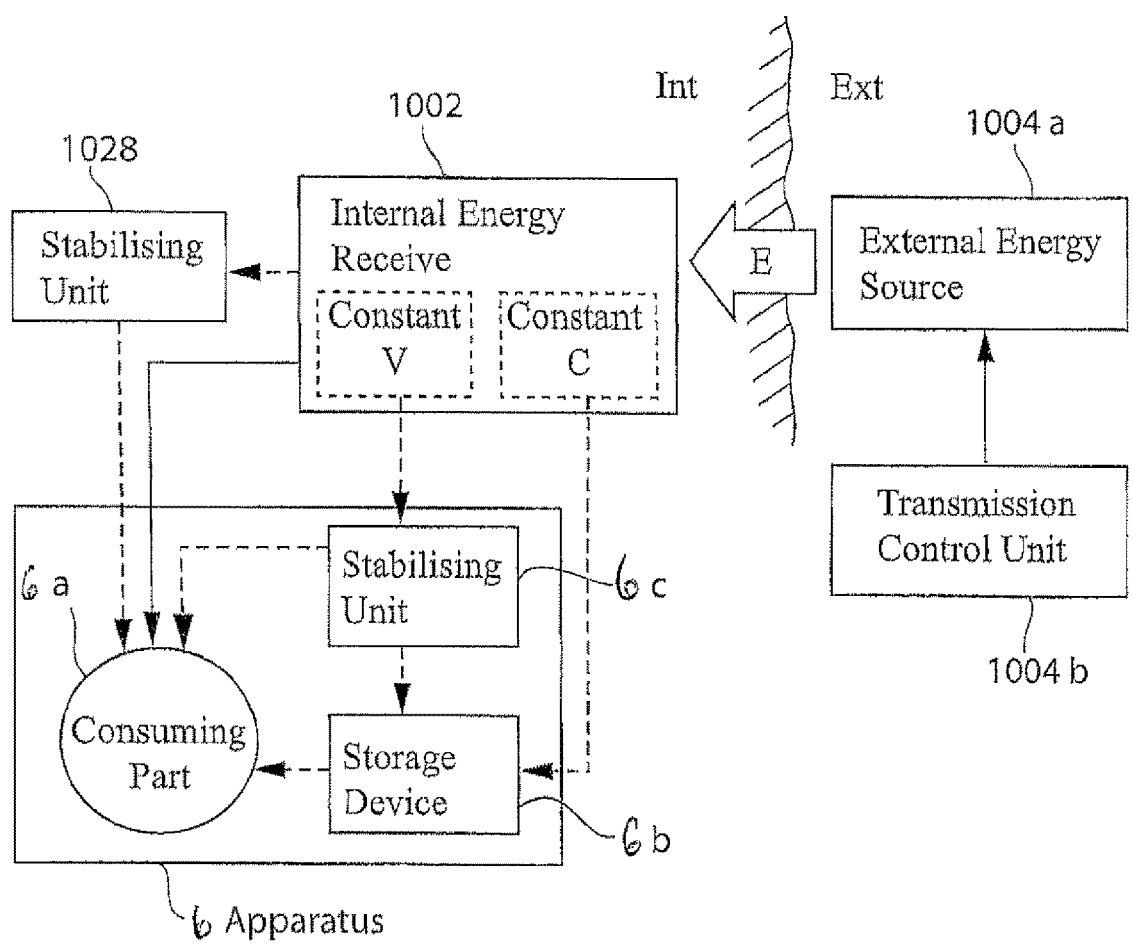
FIG. 28 is a more detailed block diagram of an arrangement for controlling the transmission of wireless energy used for the operation of the restriction device shown in FIG. 10.

FIG. 28 illustrates different embodiments for how received energy can be supplied to and used by the restriction device 6. Similar to the example of FIG. 26, an internal energy receiver 1002 receives wireless energy E from an external energy source 1004a which is controlled by a transmission control unit 1004b. The internal energy receiver 1002 may comprise a constant voltage circuit, indicated as a dashed box "constant V" in the figure, for supplying energy at constant voltage to the restriction device 6. The internal energy receiver 1002 may further comprise a constant current circuit, indicated as a dashed box "constant C" in the figure, for supplying energy at constant current to the restriction device 6.

The restriction device 6 comprises an energy consuming part 6a, which may be a motor, pump, restriction device, or any other medical appliance that requires energy for its electrical operation. The restriction device 6 may further comprise an energy storage device 6b for storing energy supplied from the internal energy receiver 1002. Thus, the supplied energy may be directly consumed by the energy consuming part 6a, or stored by the energy storage device 6b, or the supplied energy may be partly consumed and partly stored. The restriction device 6 may further comprise an energy stabilizing unit 6c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the restriction device 6, before being consumed and/or stored by the restriction device 6. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 26 and FIG. 28 illustrate some possible but non-limiting implementation options regarding how the various shown functional components and elements can be arranged and connected to each other. However, the skilled person will readily appreciate that many variations and modifications can be made within the scope of the present invention.

Figure 29:
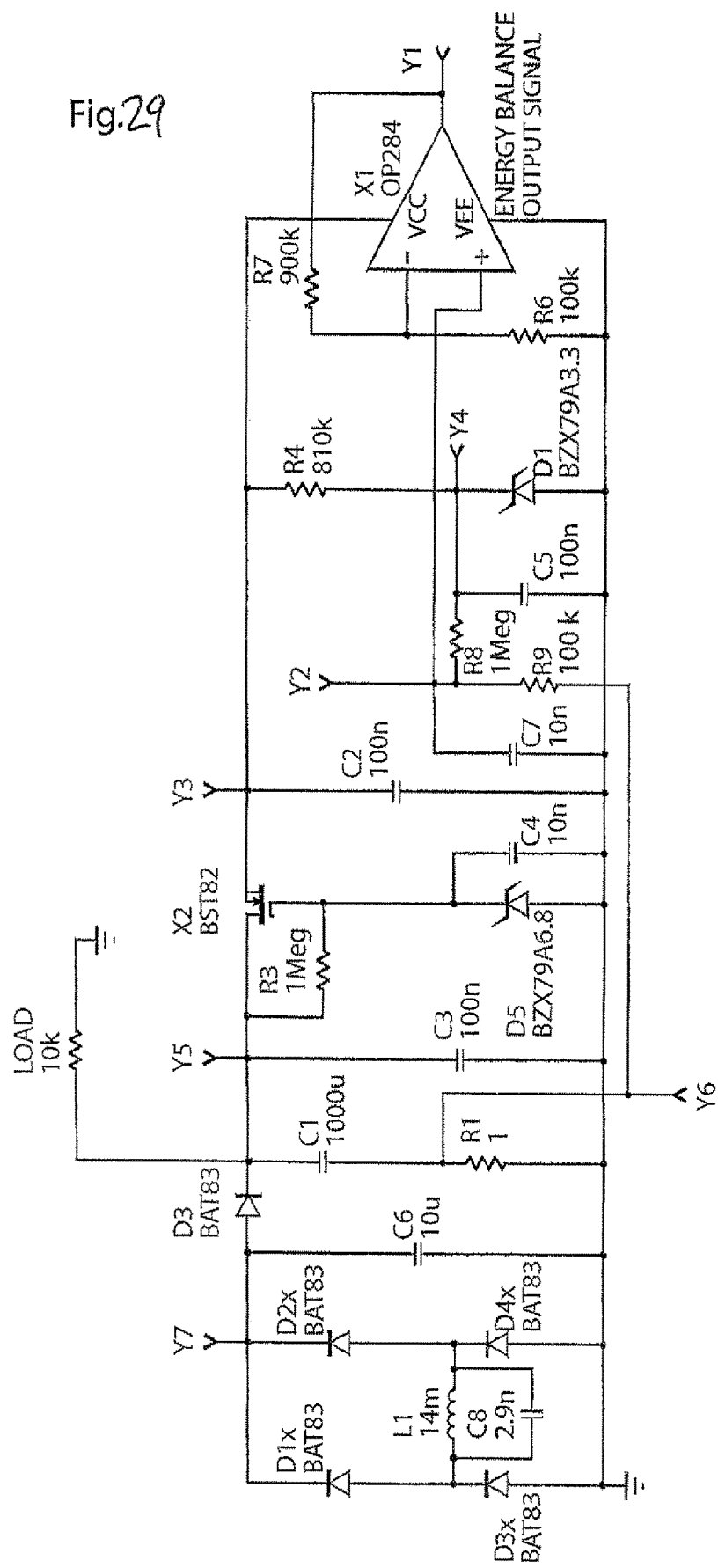
FIG. 29 is a circuit for the arrangement shown in FIG. 28, according to a possible implementation example.

FIG. 29 schematically shows an energy balance measuring circuit of one of the proposed designs of the system for controlling transmission of wireless energy, or energy balance control system. The circuit has an output signal centred on 2.5V and proportionally related to the energy imbalance. The derivative of this signal shows if the value goes up and down and how fast such a change takes place. If the amount of received energy is lower than the energy used by implanted components of the restriction device 6, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analogue system that uses comparators comparing the energy balance level with certain maximum and minimum thresholds sending information to external energy-transmission device if the balance drifts out of the max/min window.

The schematic FIG. 29 shows a circuit implementation for a system that transfers energy to the implanted energy components of the restriction device 6 of the present invention from outside of the patient's body using inductive energy transfer. An inductive energy transfer system typically uses an external transmitting coil and an internal receiving coil. The receiving coil, L1, is included in the schematic FIG. 29; the transmitting parts of the system are excluded.

The implementation of the general concept of energy balance and the way the information is transmitted to the external energy transmitter can of course be implemented in numerous different ways. The schematic FIG. 29 and the above described method of evaluating and transmitting the information should only be regarded as examples of how to implement the control system.

Circuit Details

In FIG. 29 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 12 could be incorporated in any of the embodiments of FIGS. 15-21, the hydraulic valve shifting device 1014 of FIG. 15 could be incorporated in the embodiment of FIG. 14, and the gear box 1024 could be incorporated in the embodiment of FIG. 13. Please observe that the switch simply could mean any electronic circuit or component.

The embodiments described in connection with FIGS. 26, 28 and 29 identify a method and a system for controlling transmission of wireless energy to implanted energy consuming components of an electrically operable restriction device 6. Such a method and system will be defined in general terms in the following.

A method is thus provided for controlling transmission of wireless energy supplied to implanted energy consuming components of a restriction device 6 as described above. The wireless energy E is transmitted from an external energy source located outside the patient and is received by an internal energy receiver located inside the patient, the internal energy receiver being connected to the implanted energy consuming components of the restriction device 6 for directly or indirectly supplying received energy thereto. An energy balance is determined between the energy received by the internal energy receiver and the energy used for the restriction device 6. The transmission of wireless energy F from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency.

The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an restriction device 6 as described above is thus also provided for controlling transmission of wireless energy supplied to implanted energy consuming components of the restriction device 6. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the restriction device 6 for directly or indirectly supplying received energy thereto. The system further comprises a determination device adapted to determine an energy balance between the energy received by the internal energy receiver and the energy used for the implantable energy consuming components of the restriction device 6, wherein the control device controls the transmission of wireless energy from the external energy-transmission device, based on the energy balance determined by the determination device.

In one embodiment at least one battery may be a part of or replace the energy-transforming device 1002 to supply energy to the restriction device 6 over a power supply line. In one embodiment the battery is not rechargeable. In an alternative embodiment the battery is rechargeable. The battery supply may of course be placed both remote to and incorporated in the device.

Further, the system may comprise any of the following:
A primary coil in the external energy source adapted to transmit the wireless energy inductively to a secondary coil in the internal energy receiver.
The determination device is adapted to detect a change in the energy balance, and the control device controls the transmission of wireless energy based on the detected energy balance change
The determination device is adapted to detect a difference between energy received by the internal energy receiver and energy used for the implantable energy consuming components of the restriction device 6, and the control device controls the transmission of wireless energy based on the detected energy difference.
The control device controls the external energy-transmission device to decrease the amount of transmitted wireless energy if the detected energy balance change implies that the energy balance is increasing, or vice versa, wherein the decrease/increase of energy transmission corresponds to a detected change rate.
The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
The energy used for the restriction device 6 is consumed to operate the restriction device 6, and/or stored in at least one energy storage device of the restriction device 6.
Where electrical and/or physical parameters of the restriction device 6 and/or physical parameters of the patient are determined, the energy-transmission device transmits the energy for consumption and storage according to a transmission rate per time unit which is determined by the determination device based on said parameters.
The determination device also determines the total amount of transmitted energy based on said parameters.
When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.
When the derivative is determined over time of a measured electrical parameter related to the amount of consumed and/or stored energy, the determination device determines the derivative for a monitored voltage and/or current related to the energy balance.
The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.
The electric circuit is adapted to deliver the electrical pulses to remain unchanged except varying the first and/or second time intervals.
The electric circuit has a time constant and is adapted to vary the first and second time intervals only in the range of the first time constant, so that when the lengths of the first and/or second time intervals are varied, the transmitted power over the coil is varied.
The electric circuit is adapted to deliver the electrical pulses to be varied by only varying the lengths of first time intervals between successive leading and trailing edges of the electrical pulses.
The electric circuit is adapted to supplying a train of two or more electrical pulses in a row, said train having a first electrical pulse at the start of the pulse train and having a second electrical pulse at the end of the pulse train, and
the lengths of the second time intervals between successive trailing edge of the second electrical pulse in a first pulse train and leading edge of the first electrical pulse of a second pulse train are varied by the first electronic circuit.
The electric circuit is adapted to provide the electrical pulses as pulses having a substantially constant height and/or amplitude and/or intensity and/or voltage and/or current and/or frequency.
The electric circuit has a time constant, and is adapted to vary the first and second time intervals only in the range of the first time constant, so that when the lengths of the first and/or second time intervals are varied, the transmitted power over the first coil are varied.
The electric circuit is adapted to provide the electrical pulses varying the lengths of the first and/or the second time intervals only within a range that includes the first time constant or that is located relatively close to the first time constant, compared to the magnitude of the first time constant.

FIGS. 30-33 show in more detail block diagrams of four different ways of hydraulically or pneumatically powering the implanted restriction device 6 according to the invention.

Figure 30:
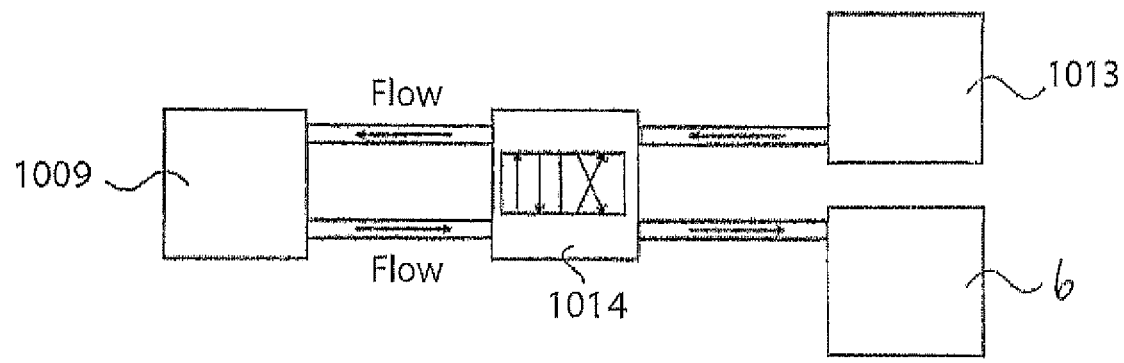
FIGS. 30-36 show various ways of arranging hydraulic or pneumatic powering of a restriction device implanted in a patient.

FIG. 30 shows a system as described above with hydraulical powering. The system comprises an implanted restriction device 6 and further a separate regulation reservoir 1013, a one way pump 1009 and an alternate valve 1014.

Figure 31:
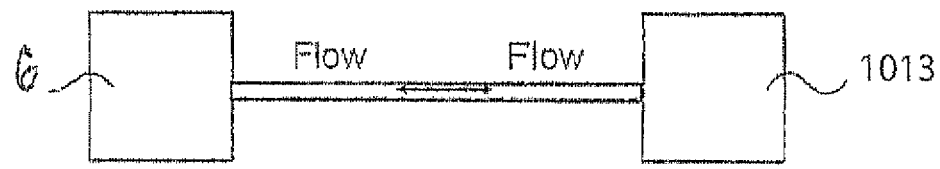

FIG. 31 shows the restriction device 6 and a fluid reservoir 1013. By moving the wall of the regulation reservoir or changing the size of the same in any other different way, the adjustment of the restriction device 6 may be performed without any valve, just free passage of fluid any time by moving the reservoir wall.

Figure 32:
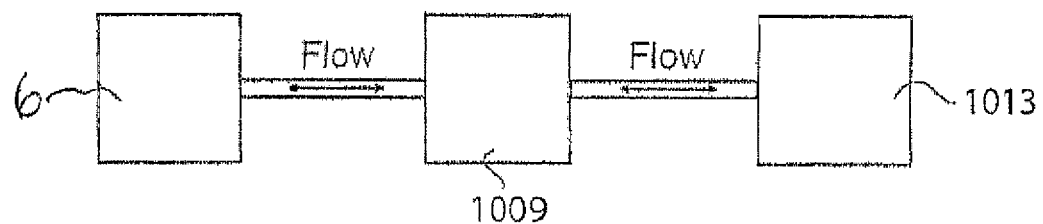

FIG. 32 shows the restriction device 6, a two way pump 1009 and the regulation reservoir 1013.

Figure 33:
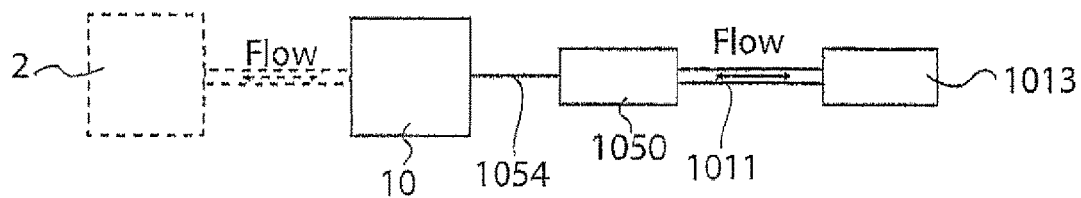

FIG. 33 shows a block diagram of a reversed servo system with a first closed system controlling a second closed system. The servo system comprises a regulation reservoir 1013 and a servo reservoir 1050. The servo reservoir 1050 mechanically controls an implanted restriction device 6 via a mechanical interconnection 1054. The restriction device 6 has an expandable/contactable cavity. This cavity is preferably expanded or contracted by supplying hydraulic fluid from the larger adjustable reservoir 1052 in fluid connection with the restriction device 6. Alternatively, the cavity contains compressible gas, which can be compressed and expanded under the control of the servo reservoir 1050.

The servo reservoir 1050 can also be part of the restriction device 6 itself.

Figure 34A:
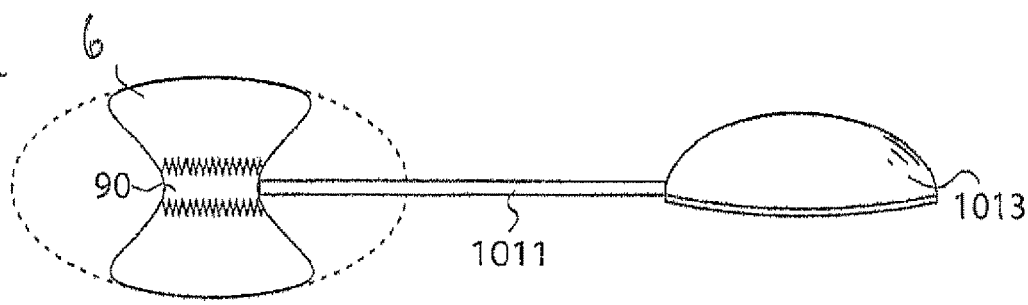
Figure 34B:
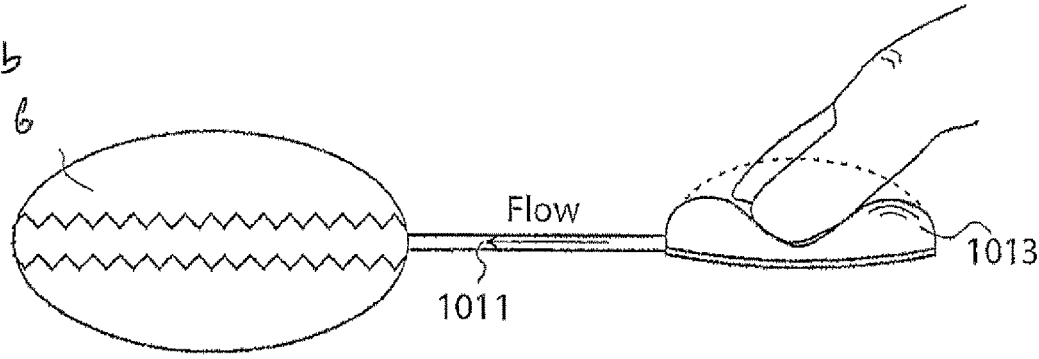
Figure 34C:
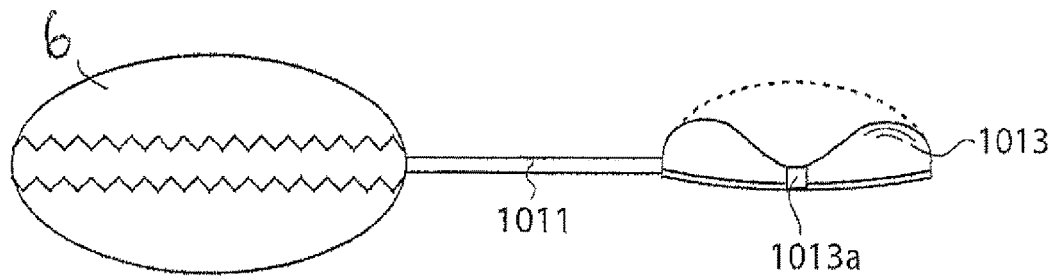

In one embodiment, the regulation reservoir is placed subcutaneous under the patient's skin and is operated by pushing the outer surface thereof by means of a finger. This system is illustrated in FIGS. 34a-c. In FIG. 34a, a flexible subcutaneous regulation reservoir 1013 is shown connected to a bulge shaped servo reservoir 1050 by means of a conduit 1011. This bellow shaped servo reservoir 1050 is comprised in a flexible restriction device 6. In the state shown in FIG. 34a, the servo reservoir 1050 contains a minimum of fluid and most fluid is found in the regulation reservoir 1013. Due to the mechanical interconnection between the servo reservoir 1050 and the restriction device 6, the outer shape of the restriction device 6 is contracted, i.e., it occupies less than its maximum volume. This maximum volume is shown with dashed lines in the figure.

FIG. 34b shows a state wherein a user, such as the patient in with the restriction device 6 is implanted, presses the regulation reservoir 1013 so that fluid contained therein is brought to flow through the conduit 1011 and into the servo reservoir 1050, which, thanks to its bellow shape, expands longitudinally. This expansion in turn expands the restriction device 6 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the restriction device 6 in a stretched position also when the user releases the regulation reservoir. In this way, the regulation reservoir essentially operates as an on/off switch for the system.

Figure 35:
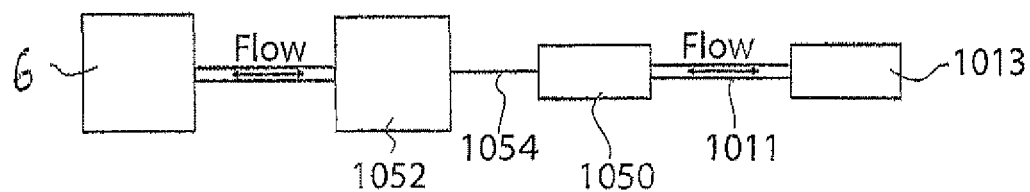
Figure 36A:
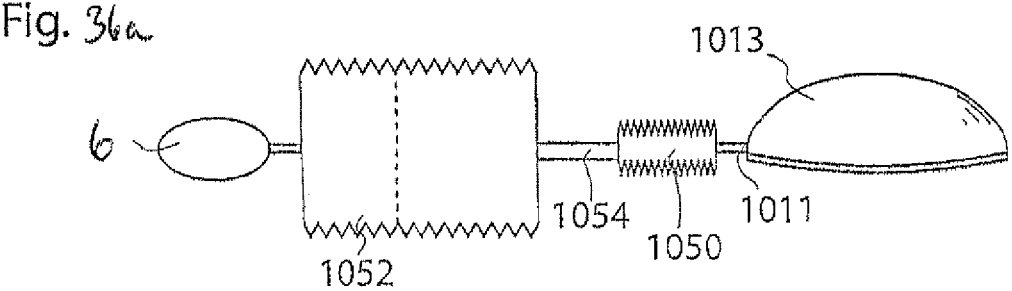
Figure 36B:
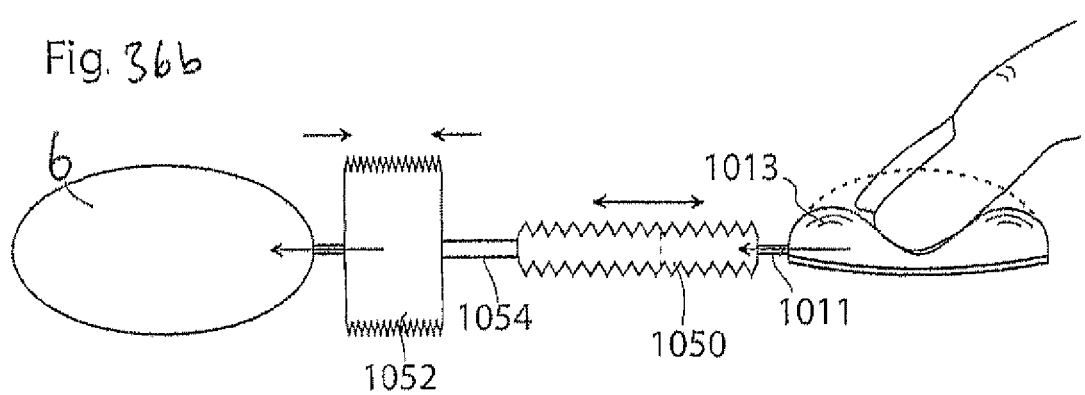

An alternative embodiment of hydraulic or pneumatic operation will now be described with reference to FIGS. 35 and 36 a-c. The block diagram shown in FIG. 35 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted restriction device 6 having an expandable/contactable cavity is in turn controlled by the larger adjustable reservoir 1052 by supply of hydraulic fluid from the larger adjustable reservoir 1052 in fluid connection with the restriction device 6.

Figure 36C:
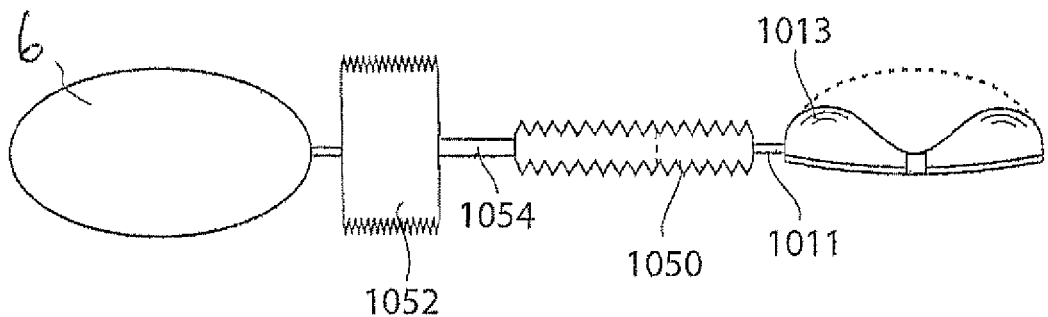

An example of this embodiment will now be described with reference to FIG. 36c hike in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 36a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the restriction device 6. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the restriction device 6. In other words, in this reversed servo, a small volume in the regulation reservoir is compressed with a higher force and this creates a movement of a larger total area with less force per area unit. hike in the previous embodiment described above with reference to FIGS. 34a-c, the regulation reservoir 1013 is preferably provided with means 1013a for keeping its shape after compression. This means, which is schematically shown in the figure, will thus keep the restriction device 6 in a stretched position also when the user releases the regulation reservoir. In this way, the regulation reservoir essentially operates as an on/off switch for the system.

Although the different parts described above have specific placements on the drawings it should be understood that these placements might vary, depending on the application.

In all of the embodiments above it is conceivable that the conduit is excluded and that the channel or channels are in direct connection with the reservoir or the injection port. Please note that any embodiment or part of embodiment as well as any method or part of method could be combined in any way. All examples herein should be seen as part of the general description and therefore possible to combine in any way in general terms.

The various aforementioned features of the method may be combined in any way if such combination is not clearly contradictory. Again, individual features of the various embodiments may be combined or exchanged unless such combination or exchange is clearly contradictory to the overall function of the method.

The invention claimed is:

1. A method for treating a female urinary incontinent patient, the method comprising the steps of:
   incising one opening in the vaginal wall of the patient;
   accessing the urethra or the neck of the urinary bladder through the opening in the vaginal wall of the patient with an instrument having a flexible tip capable of bending around at least one of the urethra or the neck of urinary bladder;
   dissecting an area in the patient surrounding the urethra or the neck of the urinary bladder with the instrument;
   implanting with the instrument at least one powered restriction device around the urethra or the neck of urinary bladder, the at least one powered restriction device comprising an elongated restriction member and forming means for forming the restriction member into at least a substantially closed loop around the urethra or the neck of urinary bladder, wherein the loop defines a restriction opening, whereby an adjustment device is configured to adjust the restriction member in the loop to change the size of the restriction opening, the at least one powered restriction device being further adapted to be connected to a rechargeable energy source or an energy receiver and thereby power the at least one powered restriction device to change the size of the restriction opening and thereby decrease the flow of urine through any of the urethra and the neck of the urinary bladder;

implanting one or both of the rechargeable energy source or the energy receiver, using a vaginal approach or using a vaginal approach in combination with a skin incision; and connecting the at least one powered restriction device directly or indirectly to the rechargeable energy source or the energy receiver, to power any energy consuming parts of the at least one powered restriction device.

2. The method according to claim 1, comprising the additional step of postoperatively adjusting said at least one powered restriction device to control the flow of urine through any of the urethra and the neck of the urinary bladder.

3. The method according to claim 1, comprising the additional step of implanting a switch and the additional step of adjusting said at least one powered restriction device using said implantable switch.

4. The method according to claim 1, comprising the additional step of adjusting said at least one powered restriction device from outside the body of the patient.

5. The method according to claim 4, wherein the method comprises the step of adjusting said at least one powered restriction device postoperatively using a remote control.

6. The method according to claim 1 comprising the additional step of implanting in the body of the patient at least one sensor adapted to measure at least one physiological parameter of the patient, said at least one sensor being adapted to send an alarm signal to the patient.

7. The method according to claim 6 wherein said at least one physiological parameter is selected from the group consisting of; pressure, volume, diameter, stretching, elongation, extension, movement, elasticity, muscle contraction, temperature or nerve impulse.

8. The method according to claim 6, further comprising the additional step of measuring at least one parameter from the list consisting of pressure, volume, diameter, stretching, elongation, extension, movement, elasticity, muscle contraction, temperature, flow and nerve impulse.

9. The method according to claim 1 comprising the additional step of implanting in the body of the patient at least one sensor that measures at least one functional parameter of said at least one powered restriction device, said at least one sensor being adapted to send an alarm signal to the patient.

10. The method according to claim 9 wherein said at least one functional parameter is an electrical parameter.

11. The method according to claim 9 wherein said at least one functional parameter is selected from the group consisting of: pressure, volume, diameter, stretching, elongation, extension, movement and elasticity, temperature or flow.

12. The method according to claim 9, further comprising the additional step of measuring an electrical parameter.

13. The method according to claim 1, wherein the method comprises implanting at least one further restriction device.

14. The method according to claim 1, further comprising the step of using cytoscopic observation of the patient.

15. The method according to claim 1, further comprising the additional step of using a cytoscopic method for placing a sensor in the patient.

16. The method according to claim 1, further comprising the additional step of using a cytoscopic method for calibrating said at least one powered restriction device.

17. The method according to claim 1, further comprising implanting at least one switch in the patient for manually and non-invasively controlling the at least one powered restriction device.

18. The method according to claim 1, further comprising implanting a hydraulic device having an implantable hydraulic reservoir, which is hydraulically connected to the at least one powered restriction device, wherein the at least one powered restriction device is adapted to be non-invasively regulated by manually pressing the hydraulic reservoir.

19. The method according to claim 1, further comprising using a wireless remote control for non-invasively controlling the at least one powered restriction device.

20. The method according to claim 19, wherein the wireless remote control comprises at least one external signal transmitter or receiver or both, and further comprising an internal signal receiver or transmitter or both implantable in the patient for receiving signals transmitted by the external signal transmitter or transmitting signals to the external signal receiver.

21. The method according to claim 19, wherein the wireless remote control transmits at least one wireless control signal for controlling the at least one powered restriction device.

22. The method according to claim 21, wherein the wireless control signal comprises a frequency, amplitude, or phase modulated signal or a combination thereof.

23. The method according to claim 21, wherein the wireless remote control transmits an electromagnetic carrier wave signal for carrying the control signal.

24. The method according to claim 21, wherein the control signal comprises one of the following: an electric field, a magnetic field, a combined electric and magnetic field.

25. The method according to claim 21, wherein the signal comprises an analogue signal, a digital signal, or a combination of an analogue and digital signal.

26. The method according claim 1, further comprising the step of using a wireless energy-transmission device for non-invasively energizing implantable energy consuming components of the at least one powered restriction device and components connected thereto with wireless energy.

27. The method according to claim 26, wherein the wireless energy comprises a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

28. The method according to claim 26, wherein the wireless energy comprises one of the following: an electric field, a magnetic field, a combined electric and magnetic field.

29. The method according to claim 26, further comprising the additional step of implanting an operation device for operating the at least one powered restriction device, wherein the wireless energy is used in its wireless state to directly power the operation device to create kinetic energy for the operation of the at least one powered restriction device, as the wireless energy is being transmitted by the energy-transmission device.

30. The method according to claim 26, further comprising the additional step of implanting an energy-transforming device for transforming the wireless energy transmitted by the energy-transmission device from a first form into a second form energy.

31. The method according to claim 26, wherein the energy-transmission device comprises a coil placed externally to the human body, further comprising implanting the energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges or second time intervals between successive trailing and leading edges of the electrical pulses or both to vary the power of the transmitted wireless energy, the energy receiver receiving the transmitted wireless energy having a varied power.

32. The method according to claim 31, wherein the electric circuit is adapted to deliver the electrical pulses to remain unchanged except varying the first or second time intervals or both.

33. The method according to claim 31, wherein the electric circuit has a time constant and is adapted to vary the first and second time intervals only in the range of a first time constant, so that when the lengths of the first or second time intervals or both are varied, the transmitted power over the coil is varied.

34. The method according to claim 1, further comprising using an external energy source for transferring energy in a wireless mode, wherein the rechargeable energy source is chargeable by the energy transferred in the wireless mode.

35. The method according to claim 34, further comprising the additional step of implanting a sensor or measuring device for sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

36. The method according to claim 1, further comprising implanting a feedback device for sending feedback information from inside the patient's body to the outside thereof, the feedback information being related to at least one of a physical parameter of the patient and a functional parameter related to the at least one powered restriction device.

37. The method according to claim 36, further comprising implanting the internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the first electronic circuit further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

38. The method according to claim 37, wherein the energy transmitter regulates the transmitted energy in response to an obtained coupling factor.

39. The method according to claim 37, wherein the external second coil is adapted to be moved in relation to the internal first coil to establish the optimal placement of the second coil, in which the coupling factor is maximized.

40. The method according to claim 1, further comprising implanting an external data communicator and an implantable internal data communicator communicating with the external data communicator, wherein the internal communicator feeds data related to the at least one powered restriction device or the patient to the external data communicator or the external data communicator feeds data to the internal data communicator or both.

41. The method according to claim 1, further comprising implanting a motor or a pump for operating the at least one powered restriction device.

42. The method according to claim 1, further comprising implanting a hydraulic operation device for operating the at least one powered restriction device.

43. The method according to claim 1, further comprising implanting an operation device for operating the at least one powered restriction device, wherein the operation device comprises a servo designed to decrease the force needed for the operation device to operate the at least one powered restriction device thereby increasing the time for a determined action.

44. The method according to claim 1, further comprising the additional step of implanting electrical components including at least one voltage level guard or at least one constant current guard or both.

45. The method according to claim 1 wherein the steps of incising and accessing include a laparoscopic method.

46. The method according to claim 1 wherein the step of accessing includes using at least one trocar.

47. The method according to claim 46 wherein at least one trocar with a diameter from 5 to 12 mm is used.

48. The method according to claim 1 wherein the step of accessing includes using at least two trocars.

49. The method according to claim 1, comprising inserting at least one laparoscopic trocar through the vaginal wall of the patient, and wherein said dissection is performed using at least one dissecting tool, which dissecting tool is inserted through at least one laparoscopic trocar.

50. The method according to claim 1, comprising dissecting a surgical site surrounding the urethra and the neck of the urine bladder to be accessed after said surgical site has been insufflated with a gas.

51. The method according to claim 1, comprising the additional step of fixating said at least one powered restriction device.

52. The method according to claim 1, comprising the additional step of fixating said at least one powered restriction device in adjacent tissue or in at least one of: an area of a) the urethra; b) the neck of the urinary bladder; c) the muscles surrounding the urethra or the neck of the urinary bladder; or d) in a tunnel of fibrotic tissue surrounding the urethra or the neck of the urinary bladder.

53. The method according to claim 52, comprising the additional step of suturing the tissue in layers.

54. The method according to claim 1, wherein the restriction is carried out at several different parts of any of the urethra and the neck of the urinary bladder.

55. The method according to claim 1, comprising the additional step of stimulating contraction in at least one of a) the urethra; b) the neck of the urinary bladder; c) fibrotic tissue surrounding the urethra or the neck of the urinary bladder; or d) the muscles surrounding the urethra or the neck of the urinary bladder; by using electricity from the energy source.

56. The method according to claim 55, comprising the additional step of stimulating in more than one location on the at least one powered restriction device.

57. The method according to claim 1, comprising the additional step of adjusting said at least one powered restriction device manually.

58. The method according to claim 1, comprising the additional step of adjusting said at least one powered restriction device non-manually.

59. The method according to claim 1, wherein the energy receiver is implanted in the abdominal cavity.

60. The method according to claim 1, wherein the energy receiver is implanted subcutaneously.

61. The method according to claim 1, wherein the energy receiver is implanted in the pelvic region.

62. The method according to claim 1, wherein the energy receiver comprises a motor or a pump that is able to use wireless energy directly to create kinetic energy to adjust the at least one powered restriction device.

63. The method according to claim 1, where the energy receiver comprises an energy transforming device transforming wireless energy to non-wireless energy.

64. The method according to claim 63, wherein the energy transforming device is powering a motor or pump directly during said wireless energy transfer.

65. The method according to claim 63, wherein the energy transforming device is used for charging an energy storage device, indirectly supplying energy to any energy consuming parts of the at least one powered restriction device.

66. The method according to claim 1 further including adjusting said at least one powered restriction device mechanically by operating a gear box and an internal control unit.

67. The method according to claim 1 further including adjusting said at least one powered restriction device hydraulically by operating a servo reservoir and a regulation reservoir.

68. The method according to claim 1 further including adjusting said at least one powered restriction device electrically by operating a motor or pump.

69. The method according to claim 1, wherein said at least one powered restriction device is implanted by a system for implantation of said at least one powered restriction device, wherein said system comprising an introductionary hose, being hollow and having at least partially a conical shape, adapted to hold said at least one powered restriction device inside the hollow space to compact the at least one powered restriction device and make it smaller and conical at a first introductionary end to ease the introduction of the at least one powered restriction device, wherein the method comprises;
mounting the at least one powered restriction device inside said introductionary hose,
introducing said at least one powered restriction device around the urethra or the neck of the urinary bladder by using said introductionary hose,
releasing said at least one powered restriction device from said introductionary hose, and
withdrawing said hose from the at least one powered restriction device.

70. The method according to claim 1, comprising the additional step of;
entering the retroperitoneal space from the vaginal opening,
placing said at least one powered restriction device in the retroperitoneal cavity,
fixating said at least one powered restriction device by a tunnel created in the fibrotic tissue in said space.

71. The method according to claim 70, comprising the additional steps of:
placing the energy receiver for receiving wireless energy subcutaneously just above the symphysis bone;
placing an electrical wire between the energy receiver and the at least one powered restriction device using said vaginal opening as an intermediate passage or using an instrument therefor through said vaginal opening; and
tunnelating the wire subcutaneously from the energy receiver to at least one powered restriction device.

72. The method according to claim 70, comprising the additional steps of:
placing the energy receiver for receiving wireless energy subcutaneously just above the symphysis bone;
placing a pump and reservoir above the symphysis bone in the abdominal cavity; and
tunnelating a hydraulic tube subcutaneously from the pump to the at least one powered restriction device using said vaginal opening as an intermediate passage or using an instrument therefor in said opening.

73. The method according to claim 70, comprising the additional step of;
introducing a camera through said vaginal opening.

74. The method according to claim 70, comprising the additional step of;
when introducing a camera through said vaginal opening, using said camera to go around the urethra and
attaching said at least one powered restriction device to said camera to thereby,
passing said at least one powered restriction device around the urinary passageway using said camera.

75. The method according to claim 1, comprising the additional step of;
entering the fibrotic tissue surrounding the urethra from the vaginal opening,
placing said at least one powered restriction device in a tunnel of said fibrotic tissue,
fixating said at least one powered restriction device by said tunnel.

76. The method according to claim 1 further including stimulating muscle tissue surrounding the urethra or neck of the urinary bladder.

77. A method involving a vaginal approach for operating urinary incontinence comprising the steps of:
incising one opening in the vaginal wall of the patient;
inserting a tube or needle through the opening in the vaginal wall of the patient into the body of the patient;
using said tube or needle to insufflate a site surrounding at least one organ selected from group consisting of: a) the urethra, b) the neck of the urinary bladder c) fibrotic tissue surrounding the urethra or the neck of the urinary bladder and d) the muscles surrounding the urethra or the neck of the urinary bladder, of the body of the patient with a gas;
inserting at least two laparoscopic trocars into said site;
inserting at least one camera through at least one of said at least two laparoscopic trocars;
inserting at least one dissecting tool having a flexible tip capable of bending around at least one of the urethra or the neck of urinary bladder through at least one of said at least two laparoscopic trocars;

dissecting in the patient an area around at least one organ selected from the group consisting of: a) the urethra, b) the neck of the urinary bladder c) fibrotic tissue surrounding the urethra or the neck of the urinary bladder and d) the muscles surrounding the urethra or the neck of the urinary bladder;

implanting at least one powered restriction device in a position around the urethra or the neck of the urinary bladder that enables it to decrease the cross-sectional area of the urethra or the neck of the urinary bladder in order to stop the movement of urine through the urethra or the neck of the urinary bladder;

implanting a rechargeable energy source, an energy receiver, or a rechargeable energy source and an energy receiver, using a vaginal approach or using a vaginal approach in combination with a skin incision; and connecting the at the least one powered restriction device directly or indirectly to the rechargeable energy source or the energy receiver.

* * * * *